United States Patent [19]

Weissleder

[11] Patent Number: 5,492,814
[45] Date of Patent: Feb. 20, 1996

[54] MONOCRYSTALLINE IRON OXIDE PARTICLES FOR STUDYING BIOLOGICAL TISSUES

[75] Inventor: Ralph Weissleder, Somerville, Mass.

[73] Assignee: The General Hospital Corporation, Boston, Mass.

[21] Appl. No.: 970,942

[22] Filed: Nov. 3, 1992

Related U.S. Application Data

[63] Continuation of Ser. No. 725,060, Jul. 3, 1991, abandoned, which is a continuation-in-part of Ser. No. 549,434, Jul. 6, 1990, abandoned.

[51] Int. Cl.$^6$ .................... G01N 33/551; G01N 33/553
[52] U.S. Cl. ............... 435/725; 128/653.1; 128/653.2; 128/653.4; 428/402; 436/173; 436/512; 436/518; 436/524; 436/526
[58] Field of Search ................. 427/2, 127; 428/402; 435/7.1, 7.21, 7.25; 436/173, 524, 525, 526, 529, 534, 538, 539, 541, 518, 512; 128/653.1, 653.2, 653.4

[56] References Cited

U.S. PATENT DOCUMENTS

| | | | |
|---|---|---|---|
| 4,672,040 | 6/1987 | Josephson | 436/526 |
| 4,795,698 | 1/1989 | Owen et al. | 436/526 |
| 4,827,945 | 5/1989 | Groman et al. | 424/4 |
| 4,859,450 | 8/1989 | Khaw et al. | 424/9 |
| 4,880,008 | 11/1989 | Lauffer | 128/654 |
| 5,314,679 | 5/1994 | Lewis et al. | 436/173 |

FOREIGN PATENT DOCUMENTS

WO90/01295  2/1990  WIPO .
WO90/01899  3/1990  WIPO .

OTHER PUBLICATIONS

Molday et al., FEBS, vol. 170, No. 2, 1984, pp. 232–238.

*Primary Examiner*—Toni R. Scheiner
*Assistant Examiner*—Christopher L. Chin
*Attorney, Agent, or Firm*—Fish & Richardson

[57] ABSTRACT

A liquid that includes monocrystalline superparamagnetic particles and a method for preparing this liquid. Also featured are a method of decreasing the NMR relaxation times of water protons in contact with biological tissue using this liquid and an in vitro method for obtaining information from biological tissue or components thereof using this liquid.

32 Claims, 16 Drawing Sheets

MONOCRYSTALLINE IRON OXIDE PARTICLES FOR STUDYING BIOLOGICAL TISSUES

This is a continuation of application Ser. No. 07/725,060, filed Jul. 3, 1991, now abandoned, which is a continuation-in-part of application Ser. No. 07/549,434, filed Jul. 6, 1990, now abandoned.

BACKGROUND OF THE INVENTION

This invention relates to collecting data from biological tissue using magnetically active compounds, more specifically, paramagnetic compounds, for magnetic resonance imaging (MRI).

Superparamagnetic polycrystalline iron oxide reagents have been used for NMR imaging. These reagents consist of multidisperse clusters of iron oxide crystals coated with, e.g., dextran, starch, albumin, or arabinogalactan to provide stability in aqueous solution. Because the size of the clusters is typically greater than 10 nanometers, they are rapidly taken up by the mononuclear phagocyte system of the liver, spleen, lymph nodes, and bone marrow following intravenous administration to permit imaging of these organs.

SUMMARY OF THE INVENTION

In one aspect, the invention features a liquid that includes monocrystalline superparamagnetic particles. Superparamagnetic particles, as defined in Bean, J. Appl. Phys. 26:1381–83 (1955) and Bean et al., J. Appl. Phys. 30:120–129 (1955), are single domain particles in thermodynamic equilibrium which exhibit a large magnetic moment and magnetic susceptibility. Typically, the magnetization curve shows no hysteresis. "Monocrystalline" refers to the fact that each particle contains a single crystal whose component parts have the same crystallographic orientation. Some polycrystalline particles introduced during manufacture of the monocrystalline particles may also be present in the liquid of the invention, but preferably at least 50% of the particles in the liquid are monocrystalline.

Preferably, the liquid exhibits a pharmaceutically acceptable level of toxicity (i.e., when administered to a human patient in an amount sufficient for diagnostic purposes, the composition does not cause death or injury to the patient). The liquid is preferably in the form of a stabilized colloidal solution, i.e., the monocrystalline particles remain suspended, (i.e., they in effect are in solution) rather than settling out over time. Such a solution is thermodynamically stable and readily reconstituted after separation of the particles from the solvent. Stabilization of MRC in aqueous solutions is preferably achieved by means of a dispersing agent (herein referenced to as an anchored surface molecule, or ASM, more fully explained below), i.e., an agent which keeps the particles from agglomerating.

The size of the monocrystalline particles is such that, when the liquid is administered to a human patient, the particles are capable of passing through the wall of a human capillary while retaining their superparamagnetic ability. Preferably, the average size of the magnetically responsive core (MRC) of monocrystalline particles is between 1 and 10 nanometers as measured by electron microscopy. Preferred particles are iron oxide particles.

As will be explained in more detail below, the use of ASM's allows the use in NMR imaging of particles which, although preferably are monocrystalline, need not be, and it can be polycrystalline where, e.g., the enhanced magnetic properties of polycrystalline versus monocrystalline particles are desired. Accordingly, the invention generally features a diagnostic agent composed of a magnetic particle with an R2 relaxivity greater than about 10 (mM sec)$^{-1}$. Preferably, the particle has an inverse spinel structure. A preferred method for making such a particle is by a process of (a) providing a mixture of iron salts having a molar ratio of $Fe+2/Fe+$ of 4:1 to 1:4, (b) increasing the pH to neutral or basic conditions, and (c) oxidizing the mixture with heat to produce the magnetic particle.

At least some of the particles in a composition of the invention may be labelled (e.g., by covalent, or, more preferably, non-covalent coupling) with one or more specific affinity labels (tissue-specific moieties, or TSM's). (As used herein, "specific affinity" means capable of being taken up by, retained by, or bound to a particular tissue or tissue component to a substantially greater degree than other tissue or tissue components; agents which have this property are said to be "targeted" to the "target" tissue or component). Following labelling of the particles, these labels retain their specific binding ability in vivo. The binding ability of the label associated with the monocrystalline particles need not be as great as that of the free label; it is sufficient that the former be capable of being taken up by, retained by, or bound to a particular tissue or tissue component to a substantially greater degree than other tissue or tissue components.

Examples of suitable TSM's include antibodies (which may be polyclonal or monoclonal) or antibody fragments (i.e. fragments which are still capable of performing the binding function, e.g., Fab fragments such as an F(ab')$_2$ fragment to myosin); antigens; monocytes, red blood cells, white blood cells, or lymphocytes; lipids (e.g., low density lipoprotein ("LDL")); polysaccharides (e.g., fructan or mannan); polysaccharides with RES specificity (e.g., arabinoxylan); polysaccharides with anti-tumor activity (e.g., galactosaminoglycan, lichen polysaccharide sulfate, antiangiogenic polysaccharide, sizofiran, polysaccharide RBS, or coriolan); or cell receptors. Also suitable are labels which are targeted to cell surfaces, e.g., plant and mammalian lectins (e.g., wheat germ agglutin); neoglycoproteins with galactose, glucose, mannose, fucose, GlcNAc, N-acetylneuraminic acid ("NANA"), glucuronic acid, lactose, melibiose, maltose, or cellobiose sugars (e.g., alpha-D-mannose neoglycoprotein); polylysine; or polyglutamate. Additionally, the specific affinity label may be targeted to cell receptors such as carbohydrate and mucopolysaccharide receptors (e.g., where the label is asialofetuin); lipid, lipopolysaccharide, and lipoprotein receptors (e.g., where the label is LDL); protein receptors (e.g., where the label is transferrin); hormone receptors (e.g., where the label is estrogen or vasopressin); or enzyme receptors (e.g., where the label is secretin). Also useful are growth factors such as interleukin-2.

The liquid and the specific affinity label may be present together, in separate containers, in the form of a diagnostic kit. In such a kit, the components are preferably in lyophilized form to facilitate storage.

The liquid of the invention can be used to decrease the NMR relaxation times ($T_1$ and/or $T_2$) of water protons in contact with a biological tissue; the liquid is administered to a human patient, who is then subjected to NMR imaging.

The method is particularly useful in imaging lymphatic, bone marrow, splenic, and hepatic tissue. When the particles are labelled with a specific affinity label as described above, particular tissues or components thereof (such as cell receptors) may be targeted for imaging.

The invention further features an in vitro method for obtaining information from biological tissue or components thereof that includes contacting the tissue or tissue component with a contrast agent that includes the above-described liquid composition and collecting the data generated by the contacting operation. Preferred data collection means include NMR imaging, NMR microscopy, autoradiography, histology, immunoblotting, and electron microscopy. Preferred tissue components include cell receptors, subcellular structures (e.g., cell nuclei, mitochondria, etc.), and cell surfaces.

The particles of the invention which are monocrystalline can be prepared by different methods including resuspension of precipitated iron oxides, direct synthesis without precipitation and synthesis in organic liquids. Purification is performed by centrifugation, ultrafiltration, osmosis, dialysis or column chromatography.

The invention provides unique, very small potent relaxation enhancing agents which can be targeted in vivo. With these agents, it is possible to obtain high contrast NMR images at low dosages; the dosage is generally a fraction of that required for conventional paramagnetic contrast agents. Due to their small size, the superparamagnetic particles readily pass through the vascular system into the interstitium, thereby facilitating uptake by the appropriate tissues. The particles are superparamagnetic despite their small size.

By labelling the agents with a specific affinity label ("target specific surface molecule=TSM), it is possible to target the labelled agent to particular tissues (e.g., diseased heart tissue, inflammatory tissue, or tumor tissue) or tissue components (e.g., cell receptors) for imaging. Because the particles are not provided with an excess of coating to improve stability, the specific affinity label may be attached directly to the particles. By using non-covalent coupling, the activity of the label is not destroyed; thus, the targeting ability is not compromised.

A further advantage of the agents is that they are stable for extended periods of time, thereby facilitating storage.

Other features and advantages of the invention will be apparent from the following description of the preferred embodiments thereof, and from the claims.

DESCRIPTION OF THE PREFERRED EMBODIMENTS

We first briefly describe the drawings.

FIG. 4 is a column chromatography plot demonstrating the ability to attach Mion to monoclonal antibody, while

The following figures are included illustrating monocrystallinity, magnetic properties and/or efficacy of MION.

Figure 11:
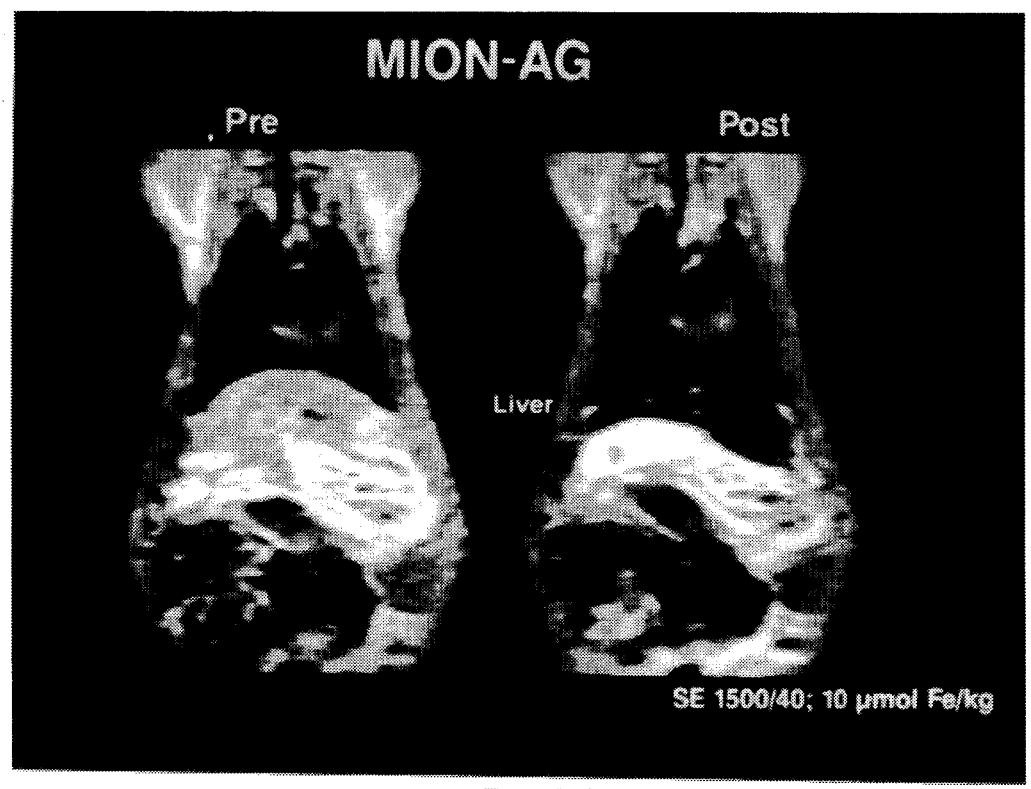

FIG. 11 is a MR image of the liver using MION-Ag, an arabinogalacatan stabilized MION having a high affinity for liver (ASG receptor on hepatocytes). After a single IV administration, the liver signal intensity greatly decreases.

Figure 12:
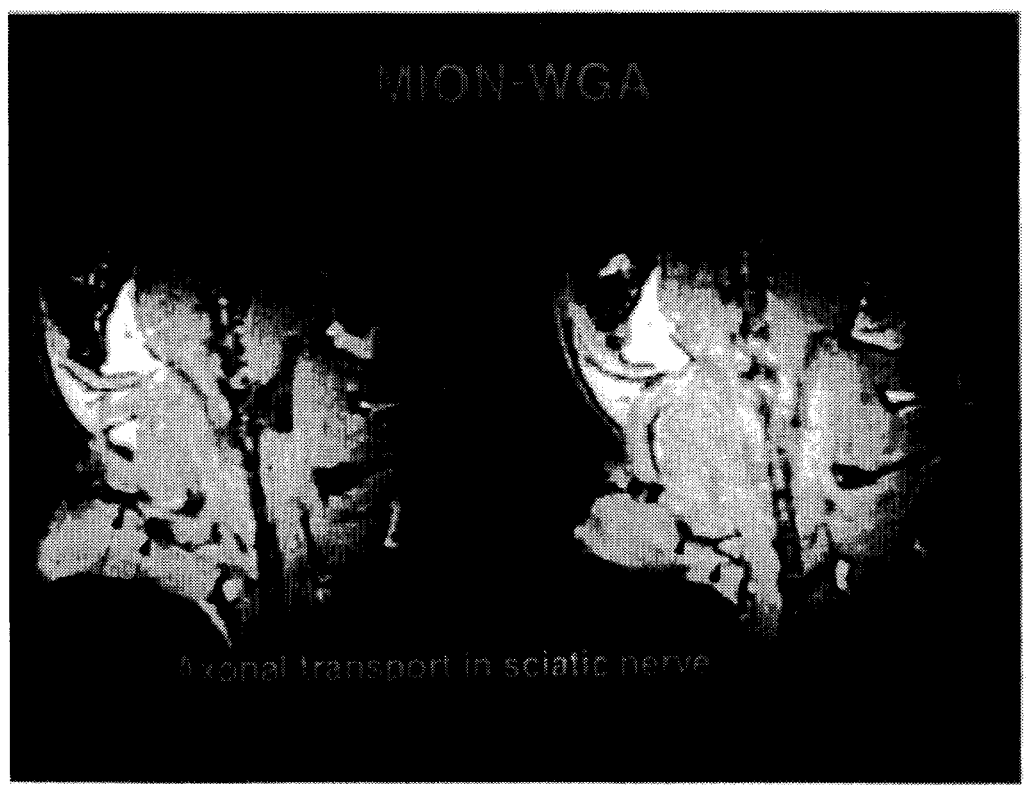

FIG. 12 is a MR image of the sciatic nerve using MION-WGA administered to the sciatic nerve via a nerve cap. Because of axonal transport of this compound, the signal intensity of the sciatic nerve decreases (arrows) and axonal transport can thus be visualized non-invasively by MR imaging.

Figure 13:
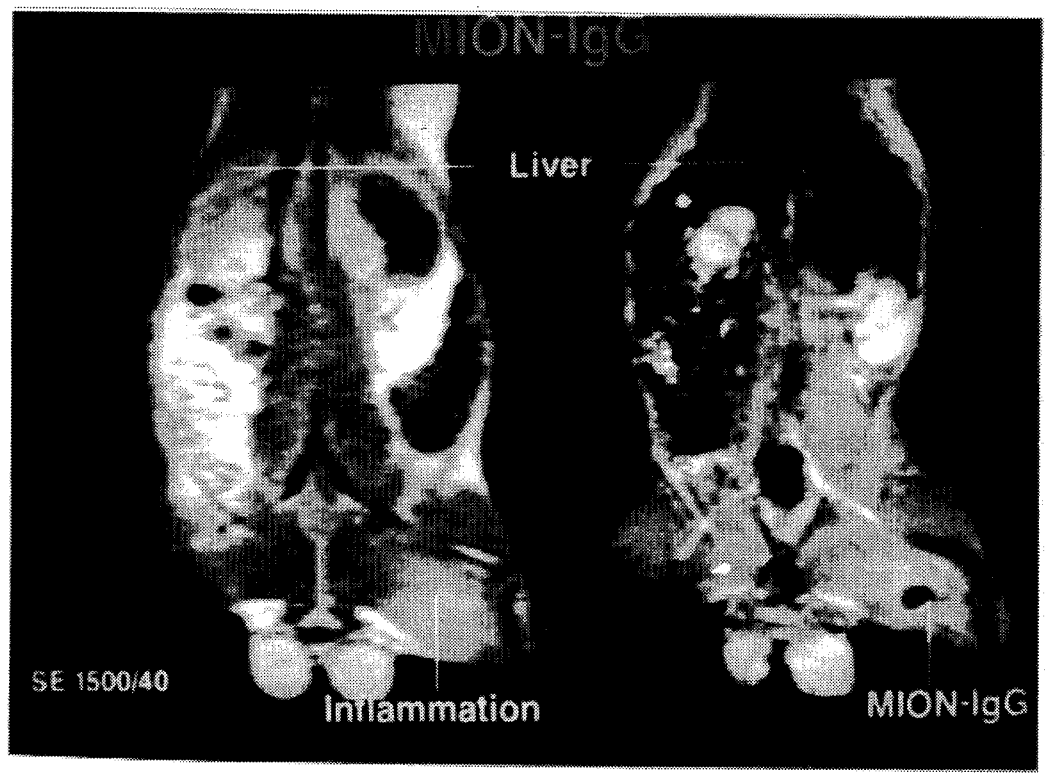

FIG. 13 is a MR image of myositis using MION-IgG. Before administration of MION, inflammation appears as bright areas on the T2 weighted spin echo image (left). Following administration of MION-IgG$^{-111}$, the compound is localized at sites of inflammation. By MR there is a consistent decrease in signal intensity in the center of the inflammation, indicating specific uptake of the MION-IgG. When unlabelled MION is injected, no such decrease in signal intensity is observed. A decrease in signal intensity is also observed in liver and bone marrow.

Figure 14:
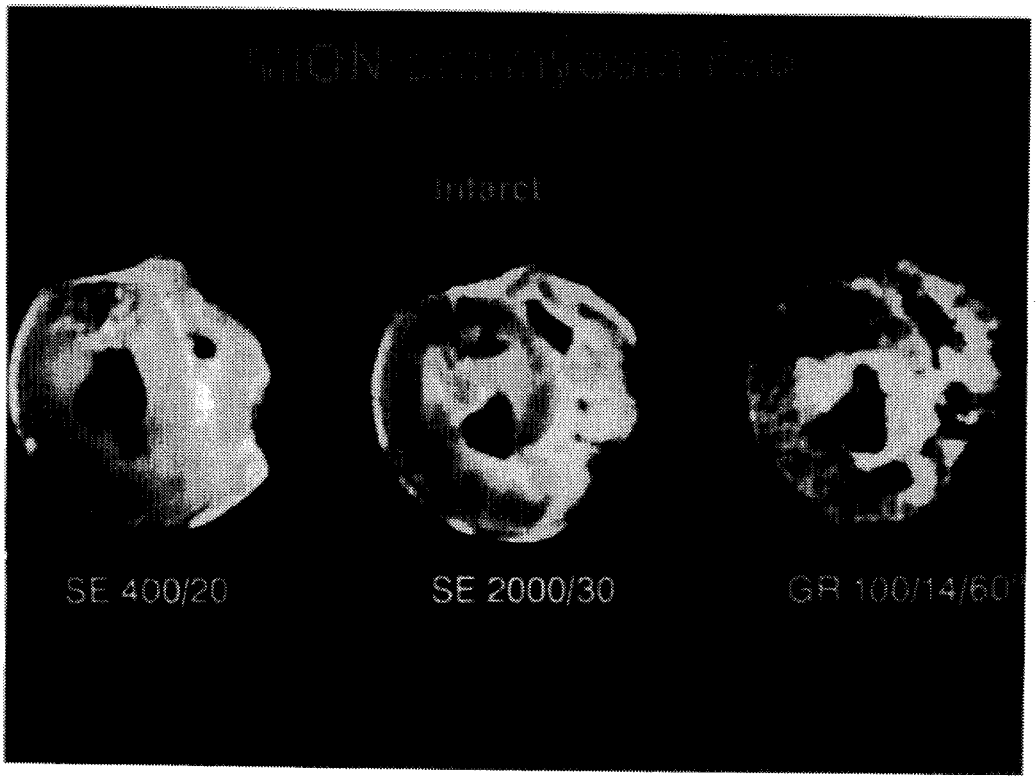

FIG. 14 is a MR image of a heart (rabbit) that has sustained a myocardial infarct using MION-antimyosin Fab administered IV. One hour after administration the heart was excised and spin echo and gradient echo MR images were obtained. These images clearly demonstrate the decrease in signal intensity in the infarct area, caused by specific deposition of MION-antimyosin Fab. This decrease did not occur in hearts injected with MION alone.

Figure 15:
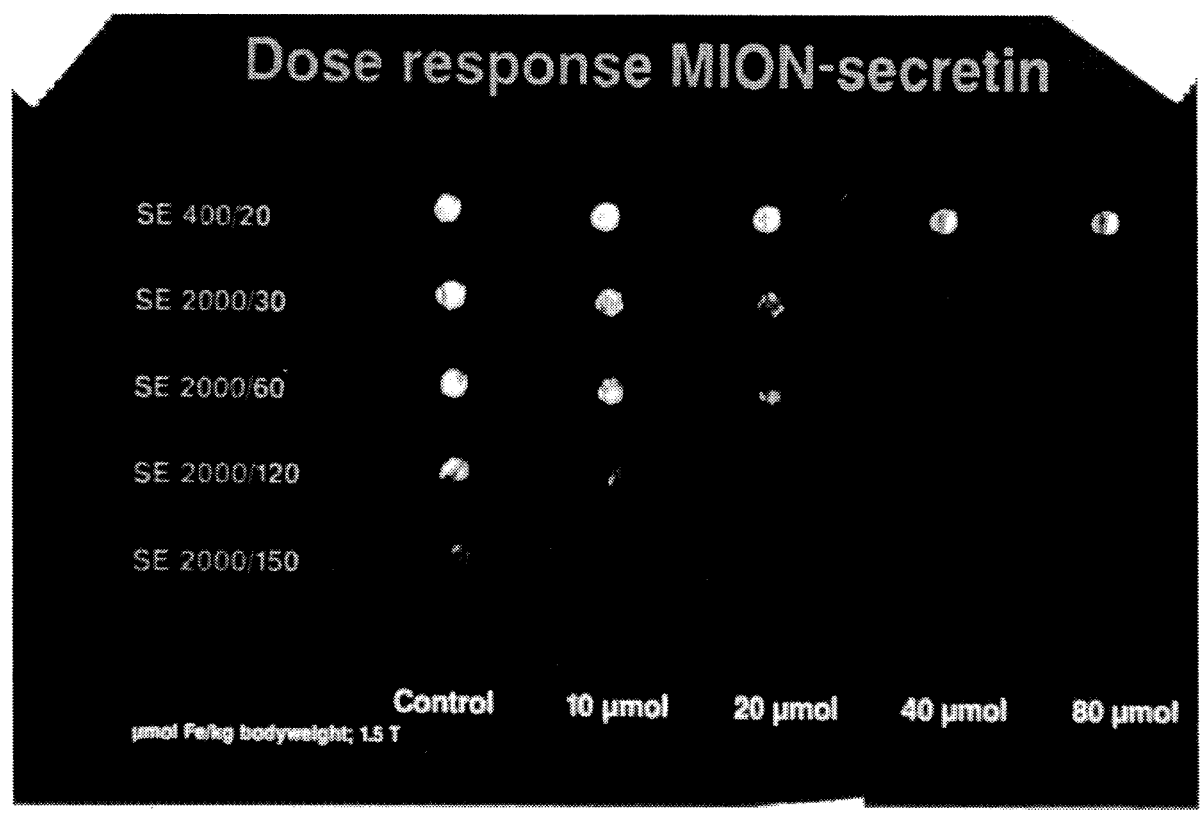

FIG. 15 is a MR image using MION-secretin/CCK administered to rats. The pancreases were harvested and stored in test tubes. The test tubes were then subjected to MR imaging. Signal intensity of pancreatic tissue was decreased with increasing doses of the contrast agent for any given pulse sequence.

Figure 16:

FIG. 16 is a MR image of femoral and tibial bone marrow using MION injected IV into a rabbit (SE 2000/30). Because MION profoundly decreases signal intensity of normal bone marrow it can be used to detect pathology.

Figure 17:
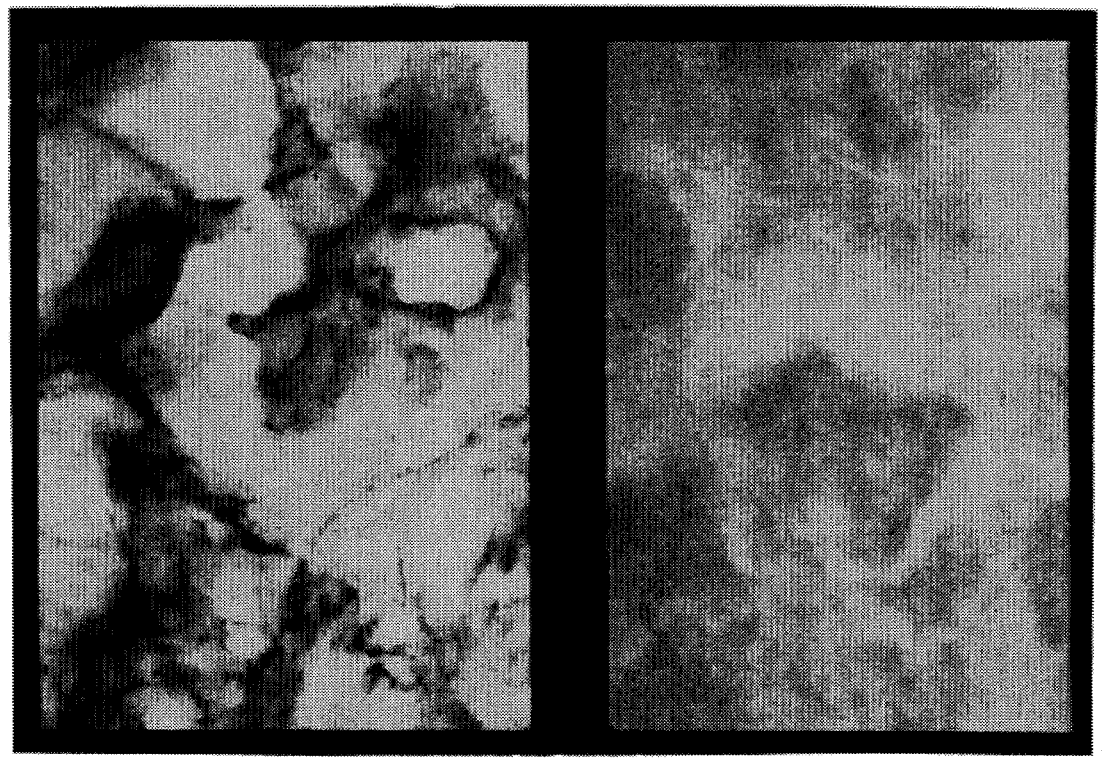

FIG. 17 shows prints of stained tissue. A modification of a histologic attachment assay was employed. In this assay, cryosectioned sections of intact tissue were incubated with MION-ASF (an asialoglycroprotein receptor agent) for 10–15 sec., washed with saline, and counterstained for iron. The print shows attachment of contrast agent to normal human liver (left, blue stain), whereas unlabelled MION does not show attachment (right, no blue stain).

Figure 18:
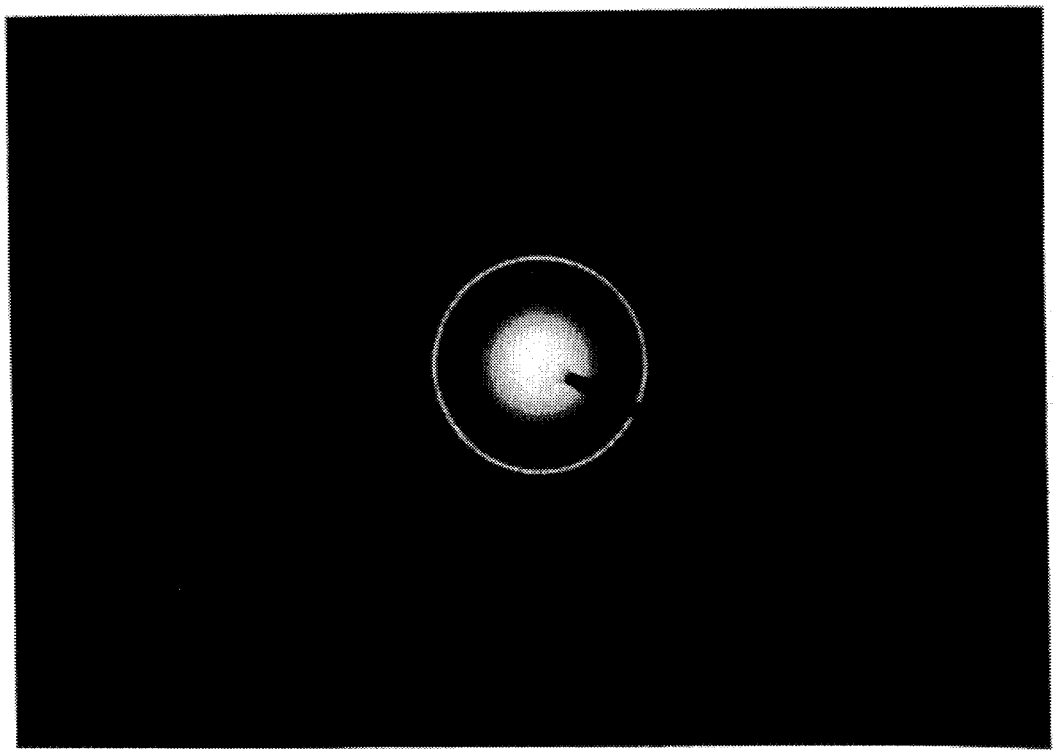

FIG. 18 is an X-ray diffraction image of MION demonstrating that the lyophilized sample contains refracting crystals of high purity. The pattern of diffraction is identical to that of magnetite.

Figure 19:
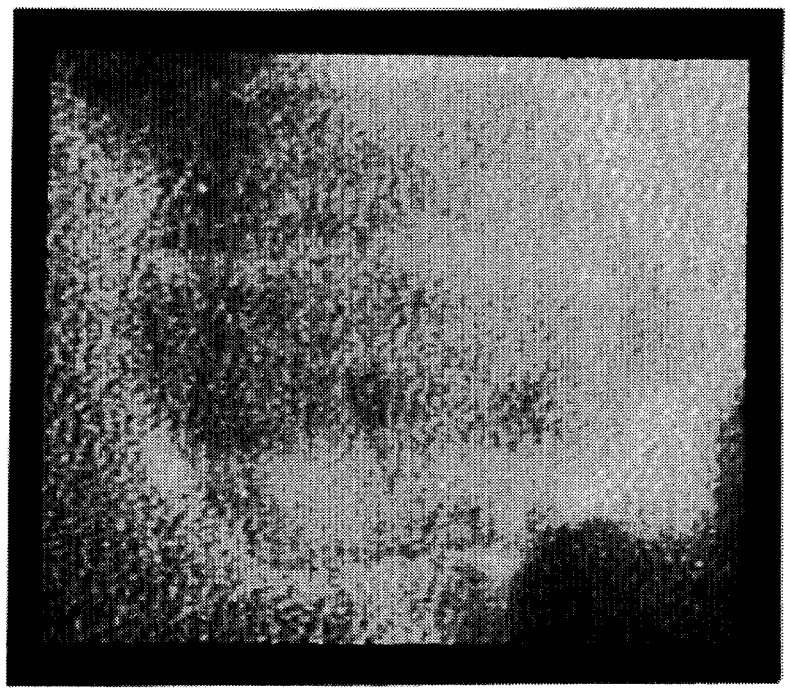

FIG. 19 is an ultrahigh resolution electron microscopy image of a MION sample with postprocessing photographic enlargement. This EM shows that MION consist of single octahedral and polyhedral crystals (monocrystallinity).

Figure 20:
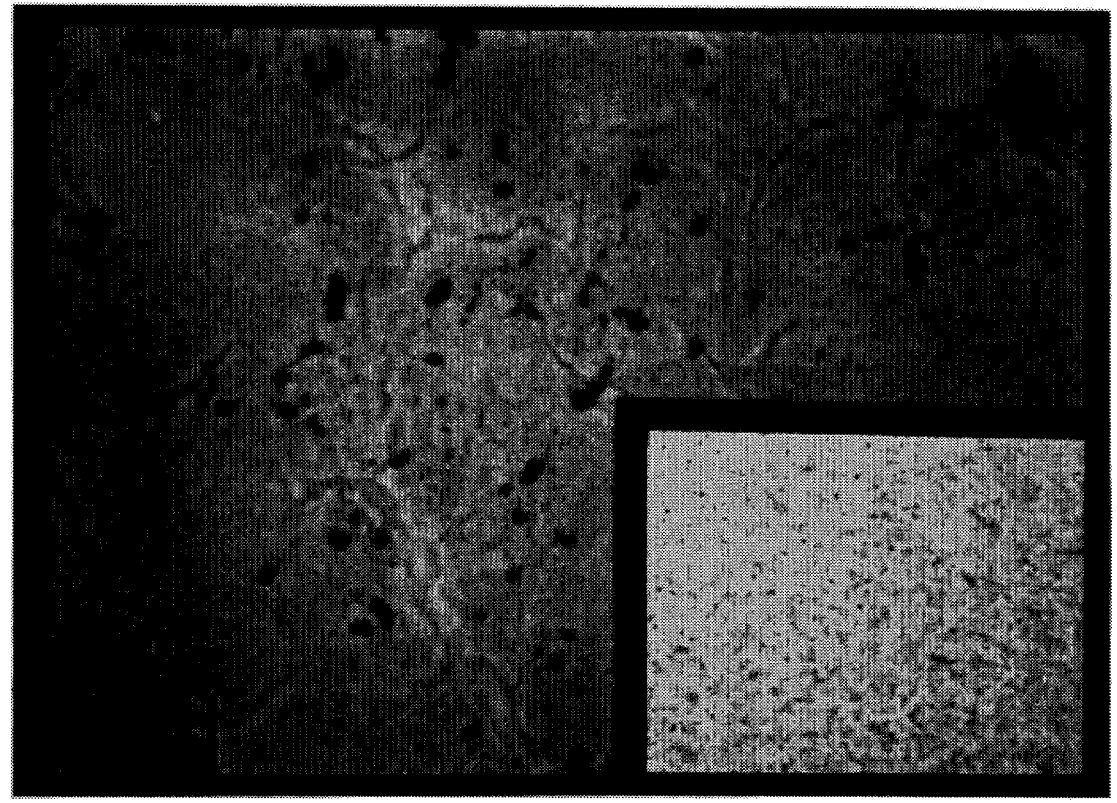

FIG. 20 shows prints of stained pancreatic tissue. Histologic sections of pancreas (rat) were incubated with MION-CCK and counterstained for iron. The dark blue deposits indicate specific attachment of this contrast agent to pancreas cells. The insert shows the control experiment with uncoupled MION where no dark blue deposits are seen.

Figure 21:
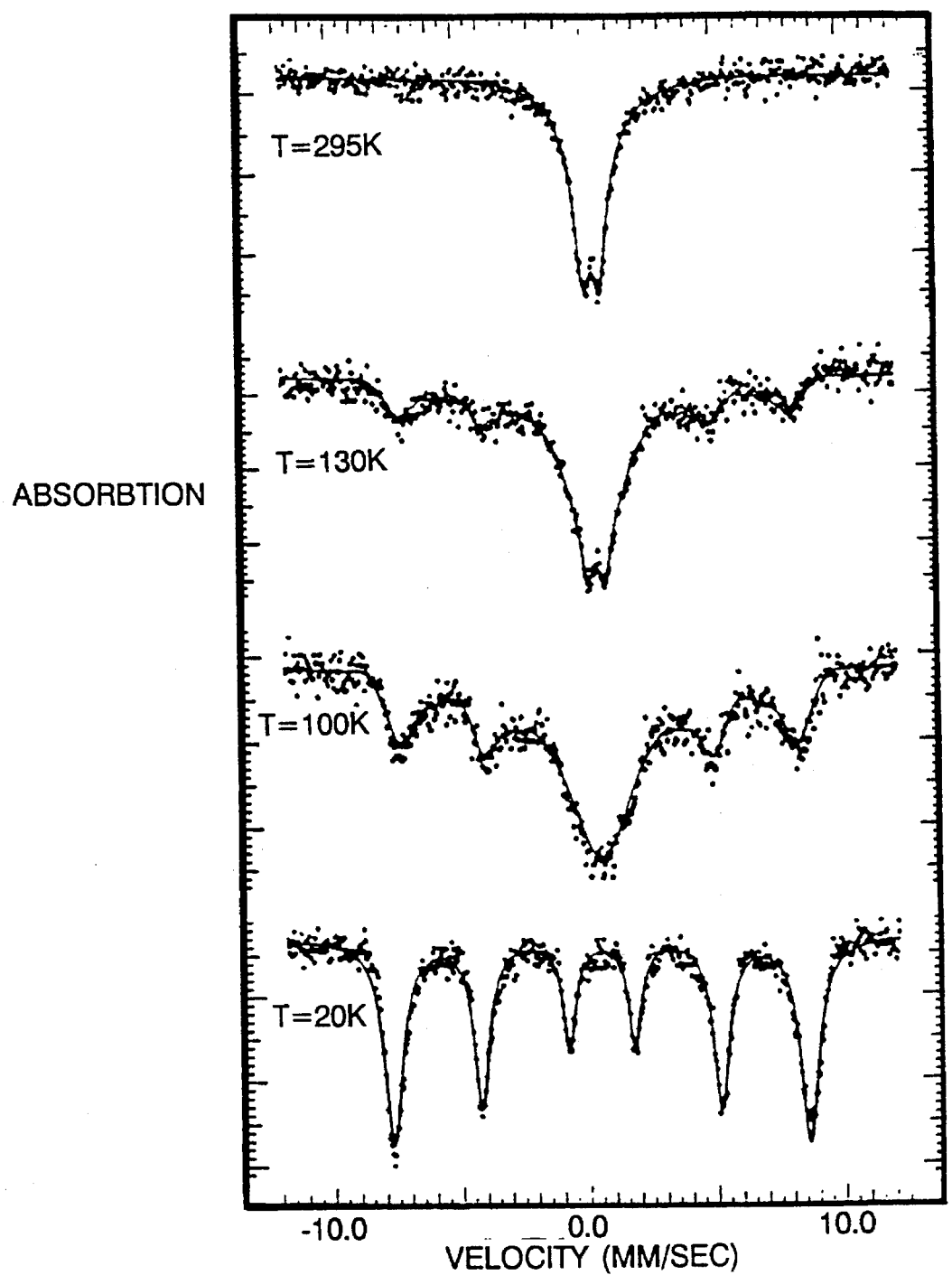

FIG. 21 is a spectrum of MION from a Mossbauer spectrometer. The anisotropy energy of MION, $K=0.8 \times 10^6$ ergs/cm$^3$ is comparable to that determined in literature for magnetite. (For 60 Å magnetite particles, it was determined that K=1.3×10$^6$ ergs/cm$^3$). This indicates that MION are smaller than 60 Å by these experiments.

GENERAL CONSIDERATIONS

The compounds of the invention generally consist of a magnetically responsive core (MRC) to which is attached an anchored surface molecule (ASM). This surface molecule is grafted onto the MRC during synthesis. In addition, a target specific molecule (TSM) may be attached to the MRC-ASM complex in order to achieve target specific imaging.

The MRC is preferably made of iron in different valency states (Fe$^{II}$, Fe$^{III}$) and oxygen which together form inorganic iron polymers or iron oxide crystals; other MRC are three dimensional graphite analogues which do not contain iron. Through the addition of anchored surface molecules (ASM), the magnetic compounds can be made soluble in water. MRC can exhibit either ferromagnetic, ferrimagnetic, superparamagnetic or paramagnetic behavior when brought into a magnetic field. The preferred magnetic behavior is superparamagnetism, which is characterized by the absence of hysteresis in the magnetization and typical behavior by Moessbauer spectroscopy. Superparamagnetism is a feature of a limited subset of iron oxides of the Fe$_3$O$_4$ magnetite type and gamma Fe$_2$O$_3$ type (maghematite). These oxides are also called "T2 agents" as they largely increase 1/T2 of tissues; this leads to decreases in signal intensity on MR images. T2 agents are also referred to as "homogeneity spoilers". When water molecules diffuse through microscopic magnetic field gradients around such particles, the protons experience efficient spin dephasing and transverse relaxation, causing a decrease in signal intensity.

The ASM modifies the MRC for biomedical use (i.e., achieving water solubility) while affecting the magnetic properties little or not at all. The ASM are firmly grafted onto the MRC surface during synthesis. ASM contain areas of hydrophilicity and may also contain areas of hydrophobicity. For medical use, ASM should be biocompatible and biodegradable.

The TSM convey specificity to the MRC-ASM complex. TSM can be linked covalently to the ASM or chemisorbed onto the MRC-ASM complex. Chemisorption to the complex is possible by partial displacement of ASM or through areas not saturated with ASM. In certain situations, the MRC-ASM complex without the TSM can be regarded as "target-specific", particularly when the ASM exhibits binding to a receptor.

In one aspect, this invention features the use of monocrystalline iron oxide nanocompounds (MION), which can be readily attached to a variety of carrier molecules by chemisorption (noncovalent binding) and thus delivered to receptor- and immunospecific sites in vivo; once attached to the target these compounds are easily detectable by MR imaging. The invention also features the use of dextran or modified dextrans as a particularly useful ASM, and the use of synthetic coating polymers for the synthesis of novel polycrystalline iron oxide preparations. The preferred synthesis with a modified MRC enables an R2 relaxivity >50 (mM sec)$^{-1}$. The synthesis extends to synthetic MRC-ASM complexes (polymer anchored iron oxide nanoparticles, PION) to be used for MR imaging.

Importance of Size

The compounds of the invention have the small sizes necessary for the interaction of the pharmaceutical with its extravascular target. Capillaries and endothelia can be classified into three groups based on the continuity of the endothelial cell linings within blood vessels. Iron oxide preparations can migrate across this endothelial barrier if certain size and surface characteristics are met. Continuous endothelia display no intracellular openings. This group can be divided into several subgroups, including continuous endothelia with pleomorphic (muscle) or purely tight junctions (brain). Very small particles (<10 nm) are able to be transported through the endothelium with pleomorphic junctions by vesicular transport. Superparamagnetic iron oxide preparations suitable for MR imaging may be too large to be transported across brain capillaries. Fenestrated endothelia (most internal organs have this kind of endothelium) either have open or closed intracellular fenestra. Very small particles are capable of "leaking" through these fenestra. Discontinuous endothelia show larger intercellular and/or transcellular openings; specialized endothelia of the latter group include sinusoids (liver, spleen, bone marrow) and the "high endothelia venules" (HEV) of lymphatic tissue. Because of these endothelial leaks, large molecular weight (MW) complexes and particles preferentially localize in these tissues.

The size of a given iron oxide preparation is important for tissue distribution and optimal drug delivery. Although for tissue distribution it is desirable to synthesize a compound as small as possible, very small size presents certain drawbacks in terms of targetability and magnetic strength of the particle. The superparamagnetic effect can be detected in particles or crystals as small as 1 nm (10Å) in diameter. Any particle above 1,000 nm will be trapped in the capillaries of the lungs during the first pass, a property that is taken advantage of in nuclear medicine lung scanning (macroaggregated albumin prepared by denaturation of human serum albumin by heat and pH). Large particles, e.g., conventional polycrystalline iron oxide aggregates, with sizes below 1,000 nm are largely phagocytosed by cells of the reticuloendothelial system (liver, spleen, bone marrow, lung) because they are too large to leave the vascular space through capillaries other than those of the discontinuous type. These large particles are therefore not targetable to other sites in the body, e.g. the pancreas, a unique feature of MION conjugates. Generally large particles have the disadvantage of rapid immunologic recognition which may elicit an immune response. Very small particles such as MION (1–30 nm) may pass fenestrated capillary endothelium, leave the space easily at sites of disrupted capillaries and reach the interstitium in large quantities. Once in the interstitium, very small particles are either specifically recognized by immunogenic sites (immunospecific imaging agents), receptors (receptor specific imaging agents), or active surface groups (lectin targeted imaging agents), or they are cleared by lymphatic fluid and eventually accumulate in lymph nodes.

As is mentioned above, the particles may be labelled (e.g., by non-covalent or covalent coupling, or by intracellular incorporation) with a variety of specific affinity molecules (TSM) in order to target specific tissues or components thereof upon administration. Non-covalent coupling is preferred because it does not interfere with the activity of the TSM and does not result in formation of toxic products. Preferably, no more than ten labels are coupled per particle to prevent the agent from becoming too large. Typically, 1–5 molecules per particle are present.

Suitable TSM are recited in the Summary of the Invention above. They include antibodies or fragments thereof, antigens, proteins, peptides, glycoproteins, neoglycoproteins, ligands for cell receptors, labels targeted at cell surfaces, lipids, polysaccharides (e.g., with RES specificity or anti-tumor activity), monocytes, and cell receptors themselves. Upon administration, the agents specifically localize in the targeted tissue, which may be healthy or diseased tissue. For example, when coupled to antimyosin, the agents accumulate in diseased myocardial tissue but not healthy heart tissue. Similarly, particles coupled to human IgG localize preferentially in inflammatory tissue. Particles coupled to a lectin (i.e. any of various proteins that agglutinate erythrocytes and other types of cells) such as wheat germ agglutin accumulate in the peripheral or axons of the central nervous system. Coupling the particles to an asialoglycoprotein such as asialofetuin targets asialoglycoprotein receptors on hepatocytes. Likewise, when coupled to growth factors such as interleukin-2, the agents target tumor cells. When coupled to lipids such as LDL, the agents are useful in diagnosing atherosclerotic disease. Particles coupled to mannan target mannan binding protein in the liver.

MION (MION)

In particular embodiments such as Examples 1 and 2, below, the monocrystalline iron oxide core has a mean mass of around 36,500 daltons, with an overall diameter of approximately 100 Å as determined by HPLC. As described above, the compound is synthesized in a procedure using a ratio of $Fe^{2+}/Fe^{3+}$ of 1:4–10 and a pH of 11–14. The MRC of this compound is believed to consist of alpha $Fe_2O_3$ and FeOOH judging by the R2 relativity (<10 $(mM\ sec)^{-1}$).

In the preferred-MION (P-MION) embodiment the MION is synthesized in a procedure using a ratio of $Fe^{2+}/Fe^{3+}$ of 2:1 at a pH 8–11. Additional modifications of organic solvents can be made to increase the homogeneity (see below). The resultant MRC consists of an inverse spinel structure (magnetite type) with a high R2 relativity (>10 $(mM\ sec)^{-1}$). MION from both syntheses can be used for target specific imaging (i.e. after attachment of additional target specific molecules) or RES imaging (i.e. unlabelled compound). The advantage of the P-MION synthesis is a much higher relativity (allows dose reduction) and a higher yield. A comparison of characteristics of the two-step synthesized MION and P-MION is summarized in the table below.

PION

Synthetic polymer stabilized iron oxide nanoparticles (PION) consist of an MRC, preferably of the magnetite type (mono-, oligo- or polycrystalline) and in addition contain a biocompatible surface anchored synthetic compound. PION can be used as unlabelled compounds for RES imaging (liver, spleen, bone marrow, lymph node) or can be targeted to specific sites through the attachment of carrier molecules (receptor and immunospecific MR imaging). An advantage of PION over dextran coated iron oxide is the elimination of potential dextran induced anaphylactic reactions (DIAR), reactions involving formation of immune complexes between circulating dextran-reactive IgG antibodies and dextran. Severe DIAR occur at an incidence of 0.002–0.013% for dextran 40 and 0.017–0.025 for dextran 60/75 (Ljunstoem KG, Renck H, Hedin H, Richter W, Roseberg B. Acta Chir Scand 1983; 149: 341–348). Severe DIAR can also be minimized by the use of low molecular weight dextrans (<5,000). These small dextrans behave as monovalent haptens. They react with dextran reactive immunoglobulin (IgG) without bridge formation and therefore with no tendency for the formation of large immune complexes. A polyvalent hapten may form complexes with antibodies as antigen does, but a monovalent hapten can only bind to individual combining sites of antibodies, therefore eliminating the pre-requisite for immune complex formation.

SYNTHESIS—GENERAL

Magnetically responsive core (MRC)

The synthesis of superparamagnetic iron oxide compounds involves solubilizing $Fe^{2+}$ and $Fe^{3+}$ in water and adding a polymer (which is to be grafted onto the iron oxide surface) to this solution. The ratio of $Fe^{2+}/Fe^{3+}$ is crucial for the formation of different types of superparamagnetic iron oxides (see table).

|  | MION | P-MION |
| --- | --- | --- |
| Chemistry | | |
| Mass | 36,500 | $10^4$–$10^9$ |
| Structure | monocrystalline | mono-, di-crystalline |
| Size | 3nm | <20 nm |
| Coating | low MW dextrans, others | modified dextrans, polysaccharides, synthetic polymers |
| Charge | negative | depends on ASM |
| Fe2+/Fe3+ ratio | 1:4 | 2:1 |
| pH adjustment | NaOH | NaOH |
| Buffer | Tris-saline | Tris-saline, meglumine |
| Chem structure | composite** | Organomagnetite, composite |
| Magnetic | | |
| R1 | 1–10 | 1–30 |
| R2 | 1–10 | 10–200 |
| B at 1.5 T | 30.50 | |
| In vivo behavior | | |
| BLood T1/2 | 30–60 min | 30 min.–several hours |
| Biodistribution | RES and targets | Biodistribution can be tailored |
| Receptor imaging | liver and pancreas | Extrahepatic receptor imaging proven |
| Immunospecific imaging | yes | Concept and feasibility proven |

**formula: $(Fe_3O_4)n(Fe_2O_3)m$ (n = 0–1,000; m = 0–1,000); FeOOH,
***formula of organomagnetite: $(Fe_3O_4)n$ = Y where Y is IgG for example

| Paramter | Magnetite | Maghematite | Hematite | Oxyhydroxide |
|---|---|---|---|---|
| Formula | $Fe_3O_4$ | $—Fe_2O_3$ | $\alpha\text{-}Fe_2O_3$ | FeOOH |
| Color | black | brown | brown | brown |
| Magn strength* | 4 | 4 | 0–0.01 | 1–2 |
| Crystallography | inverse spinel | inverse spinel | Hexagonal closed packed (HCP) | cubic closed packed |

*Bohr magneton/unit formula

The pH of the starting solution is acidic because iron salts in aqueous solutions act as acids. The pH is then slowly increased to neutral or alkaline milieu. During the increase in pH different intermediary iron complexes form. These initial reactions are preferably performed at or below room temperature to ensure ordered formation of complexes. At pH 2–4 a complex forms and at pH 6–9 a green compound forms. The structure of these intermediary compounds has been described. Synthesis involves the oxidation of the green complex by heat; in the modified syntheses the MRC are precipitated by high pH or an organic solvent and is later resuspended in aqueous solutions.

| pH | color | Structure |
|---|---|---|
| 1–3 | yellow/brown clear | aqueous solution |
| 2–4 | | inorganic polymer I |
| 6–9 | green suspension | inorganic polymer II |
| 9–14 | black slurry | iron oxides | polymer I: $[Fe^{2+}_2 Fe^{3+}_1 O_x (OH)_y]^{(7-2x-y)+}$ polymer II: $[Fe^{2+}_1 Fe^{3+}_2 O_x (OH)_y]^+$ Misawa T., J. Inorg. Nucl. Chem, 1973; 35: 4167–4174;
Misawa, T., J. Inorg. Nucl. Chem., 1973; 35: 4159–4166.

The initial reaction steps are believed to be described by the following formulas:

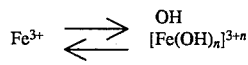

[Fe(OH)$_n$]$^{3+n}$ —— Inorganic polymer (gel)

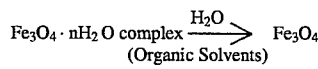

The initial inorganic polymer backbone is known as Cotton and Wilkinson.

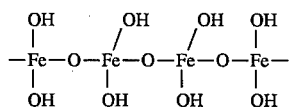

This linear compound may form cross links with $Fe^{II}$ salts. One of many possible chemical structure of this cross linked intermediary precipitate is:

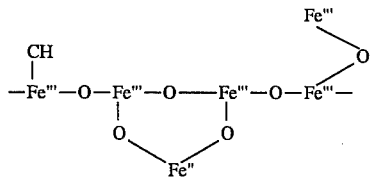

After oxidation of the intermediary complexes $Fe_3O_4$ (magnetite), alpha-$Fe_2O_3$, or FeOOH (iron oxyhydroxide) forms. The crystalline structure of $(Fe_3O_4)n$ is one of an inverse spinel structure with cubic unit cell containing $[Fe^{3+}(Fe^{2+}) Fe^{3+}O_4]_8$.

Anchored surface molecules (ASM)

Suspending agents can be grafted onto the particle surface if these compounds are available in solution during the formation of the MRC. Late addition of polymeric suspending agents to precipitated iron oxides results in light, reversible attachment (chemisorption), a technique which is used for the attachment of carrier molecules to the MRC-ASM complex. ASM are attached to iron oxides to a) achieve high solubility in aqueous solution, b) stabilize the compound in solution so that the compound remains in solution over long periods of time, preferably two months or longer, and c) to decrease easy immune recognition of the compound once injected intravenously. ASM can be attached to multiple sites (surface groups); most common reactions involve covalent bonding of iron hydroxyl groups with silicates, phosphates, sulfates, or carbon:

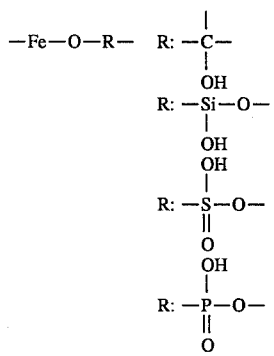

Another embodiment is the noncovalent grafting of organic groups bearing hydroxyl, carboxyl, aldehyde, sulphur groups to the iron oxide:

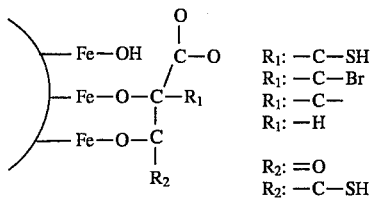

$R_1$: —C—SH
$R_1$: —C—Br
$R_1$: —C—
$R_1$: —H $R_2$: =O
$R_2$: —C—SH

Mechanism of action

The two forms of protective coatings are surface bound ionic coatings and surface bound polymeric coatings with hydrophilic (and hydrophobic) groups. Ionic coating achieved by grafting of carboxylic acids (negative charge) or amines (positive charge) causes repulsion of individual particles by Coulombic forces.

Polymer grafting exerts a Rebindez's effect: the osmotic pressure in areas of aggregated particles is higher than in surrounding areas keeping particles apart. This colloidal phenomenon of steric stabilization creates a repulsive steric barrier (anti-adhesive effect).

Preferred ASM
Synthetic compounds

The following synthetic compounds are preferred molecules to be anchored to MRC's:

- Polymers and copolymers
  - polyoxyethytene sorbitan esters ("polysorbates 20–80") esp. monotaurate, monoleate, monopalmitate, monostearate esters and polysorbate-80
  - polyoxyethytene and polyoxypropylene derivatives (esp. poloxamers, poloxamines dn tetronics); see structural formula below
  - non-ionic surfactants
  - polyoxyl stearates (35–80)
  - polyvinyl alcohols
  - polymerized sucrose
  - polyhydroxylalkylmethacrylamides (alkyl=proply, ethyl, . . . etc.)
  - lactic acid and glycolic acid copolymers (polylactide-coglycolide)
  - polyorthoesthers
  - polyalkylcyanoacrylates
  - polyglycerol surfactants (such as described by Handjani-Vila, Int J Cosmet Sci 1979; 1:303)
  - polyhydroxylated polyvinyl matrices (such as described by Ferruti, Frontiers of Macromolecular Science, Blackwell Scientific Publication, 1989: 455–461)
  - polyhydroxyethylaspartamide
  - polyaminoacids, esp. polylysine
  - styrene-maleic acid copolymers
  - polycaprolactones
  - polyanhydrides
- Starch derivatives
  - starch-2-hydroxymethyl ether (hetastarch)
  - hydroxyethyl starch
- Dextran
  - galactosylated dextran with and without the use of spacer molecules for attachment
  - lactosylated dextran
  - aminated dextran
  - dextran with -SH groups
  - dextran with carboxyl surface groups
  - dextran with aldehyde surface groups
  - dextran with other reactive surface groups
  - biotinylated dextran

- Cyclodextrin
  - beta-cyclodextrin
  - hydroxypropyl-cyclodextrin
- Other Compounds
  - fatty acids, their salts and derivatives: esp. sodium lauryl sulphate, sodium stearate, stearic acid, sorbitan monolaurate, sorbitan monoleate, sorbitan monopalmitate, sorbitan monostearate
  - sterols, digitogenin, saponins and their derivatives
  - lecithins
  - mono-, di-, triglycerides and their derivatives
  - octoxynol
  - tyloxapol and derivatives Most preferred ASM are dextrans, modified dextrans, polyoxyethylene sorbitan esters; polyoxyethylene and polyoxypropylene derivatives; polymerized sucrose; fatty acids; and mono-, di-, and triglycerides and their derivatives. Two representative structural formulae are given below.

Poloxamer:

$$HO{+}C_2H_4O{+}_a{+}C_3H_6O{+}_b{+}C_2H_4O{+}_aH$$

Polysorbate 20:

Natural polysaccharides

Any water-soluble oligo- or polysaccharide can be used for attachment. Preferred polysaccharides are large enough to exert the Rebindez effect (MW>1,000) and small enough to be non-immunogenic (MW<20,000). Some polysaccharides also convey target specificity to the iron oxide compound, e.g., galactose-containing polysaccharides are taken up by galactose specific lectins in the liver (see below). Preferred polysaccharides include:

- homopolysaccharides
  - dextrans and modified and substituted dextrans
  - modified dextran, esp. diaminoethane derivatized dextran (additional compounds described by Ferruti, Forttiers of Macromolecular Science, Blackwell Scientific Publication, 1989: 455–461)
  - beta-cyclodextrins
  - galactans
  - mannans
- heteropolysaccharides
  - neutral group
    - galactosylated dextran
    - arabinogalactans
    - galactomonnans
    - glucomannans
  - acidic group
    - plant gums: agar, acacia, gum arabic, traganth
    - seaweed mucilages
    - agar
    - fucoidan
  - alkaline group (amino-polysaccharides)
    - chitosan
    - hyaluronic acid
    - chondroitin sulfate
    - heparin Anionic compounds Preferred compounds include:

Inorganic
- polyphosphates
- polysulfates

Organic
- poly-carboxylic acids (e.g., citrate)
- polyamino- or poly-carboxylic acids Target specific molecules (TSM)

TSM are attached to the MRC-ASM complex to convey target specificity to the compound. Attachment is achieved either by chemisorption or by covalent attachment.

Chemisorption of polyhydroxyl groups containing TSM to MRC-ASM

The surface (≈7–15 Å) of an iron oxide crystal is disordered, i.e., the surface is not the same as in the core. Free $Fe^{3+}$ on the particle surface reacts with water and forms Fe-OH bonds. In alkaline milieu Fe-$O^-$ groups form, whereas in acidic pH $Fe^+$ surface groups are present. Even in neutral milieu negative and positive charges are present which then react with OH groups of polyhydroxyl compounds (polysaccharides, polyalcohols, etc).

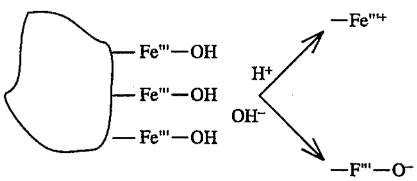

These interactions result in strong building between polyhydroxyl compounds and the iron oxide surface.

Attachment of protein type TSM to MRC-ASM

Proteins may interact with Fe-OH groups in a variety of ways. These interactions are based on electrostatic forces and complex formation. For example, aspartic acid, asparagine, and glutamic acid bind to the iron via the carboxyl group. Lysine, arginine, histidine bind via the amino group. Bonds may also form by hydroxyl groups (serine, tyrosine) and sulfur groups.

Pure electrostatic interaction is seen with positively charged amino groups:

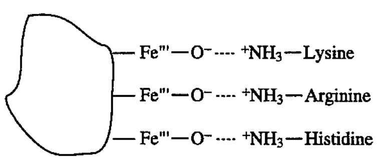

In the case of carboxylic acids, the interaction is also electrostatic, but in addition there apparently is some complex formation:

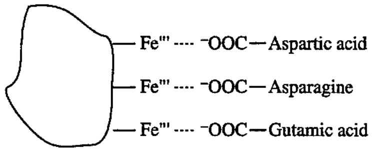

Complex formation is typical with sulphur and oxygen groups. The energy of binding forces determines whether the bond is covalent or non-covalent. For example, Fe -S bonds are high energy bonds and the interaction may be regarded as covalent.

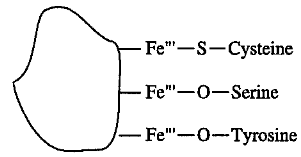

The multitude of interactions allows complex formation among many protein residues and the iron surface. Whereas the electrostatic force of each complex is weak, the multitude of complex formations results in tight binding. The binding constant of protein on iron oxide is given by:

$$K \approx K \times e^{nE}$$

Where n is the number of reacting groups, E is the binding force (constant), and Ko is a constant. Simplified, this formula indicates that the binding constant increases exponentially with the number of complexed groups.

Covalent attachment of TSM to MRC-ASM

A variety of chemical syntheses may be used to covalently attach target specific molecules (TSM) to ASM. One successful technique has been the partial oxidation of ASM-OH groups to aldehyde groups using the periodate method. Aldehyde groups then react with amino groups of proteins.

MION Synthesis

MIONS can be made using either of two different processes (see MION synthesis and preferred MION synthesis). The first step is solubilization of iron salts at appropriate ratios in the presence of an ASM, e.g., dextran. In a second step the pH of this solution is raised and iron oxide solutions form as described in Spiro et al., J. Am. Chem. Soc. 89: 5555–65 (1967); Molday et al., J. Immun. Meth. 52: 353–67 (1982); and Molday et al., FEBS Lett. 170: 232–38 (1984). In this application, several modifications and alternate synthesis routes are featured to ensure production of stable, soluble monocrystallites. These modifications will become apparent in the following examples:

EXAMPLE 1

2 g $FeCl_3.6H_2O$ and 0.30 g $FeCl_2.4H_2O$ were dissolved in 100 ml of 1M aspartate or citrate solution to which 7.5g of dextran (molecular weight=9,400) had been added. Dissolution was carried out at 90° C. under continuous stirring. When dissolution was complete, the pH of the solution was approximately 0.2. Under continuous stirring the pH of the solution was gradually raised to 11–14 by addition of 10M NaOH. When the desired pH was reached, black iron oxide particles precipitated, and sonification was carried out at 90° C. at 60 W for 30 minutes and the precipitate was resuspended in a dispersing solution. The next steps were:

- centrifuge the slurry at 2,500 RPM for 5 minutes and decant supernatant;
- prepare the dispersion solution: 88.2 g of sodium citrate (and 7.5g of dextran) in 300 cc of water;
- dissolve the slurry in the dispersion solution at 80° C.; adjust the pH to 8.

Next, the iron oxide particles thus obtained were placed in a form suitable for intravenous administration to a patient. This involved the following sequential steps: 1) ultracentrifugation, 2) sonification, 3) column separation, 4) ultraconcentration, and 5) dialysis.

Centrifugation removes large iron oxide particles; such particles typically are in the 50–2000 nanometer range. The sample was centrifuged at 13,000 g for about 1 hour to complete the separation. Alternatively, the iron oxide slurry may be successively filtered through a series of microfilters (pore diameters of 450 nm and 200 nm).

Next, the slurry was sonicated to disperse the remaining particles prior to fractionation in order to increase the efficacy with which the final iron oxide particles are obtained. Sonification was carried out in a Branson sonifier at 30 watts for 30 minutes for a 100 ml slurry sample.

The sonicated slurry was subjected to column separation to separate monocrystalline particles from ultrasmall polycrystalline particles. Separation was performed by loading approximately 12 ml of the slurry onto a Sephadex column capable of separating high molecular weight compounds (e.g., a $CL_4$-Sephadex column commercially available from Pharmacia, Uppsala, Sweden); typically, a 45 cm column is sufficient. The column was equilibrated with 0.1M aspartate or citrate buffer at pH 7.4, after which a total of 80 fractions were collected. The respective molecular weights of the fractions were determined using molecular weight standards.

The column separation step may be eliminated by ultracentrifuging the slurry for a longer period of time, e.g., about 3 hours instead of 1 hour. The extended ultracentrifugation alone is sufficient to remove the polycrystalline particles.

The fraction containing particles whose diameters were within the range 1–5 nanometers was then ultraconcentrated in a stirred cell (AMICON) or vacuum dialysis apparatus, and then dialyzed. Dialysis is required to 1) remove toxic heavy metal ions, 2) remove excessive salt, 3) reduce the aspartate or citrate concentration of the sample to reduce toxicity, and 4) achieve a higher reactivity with specific affinity reagents on a gram of iron basis if such labelling is performed. Dialyze the MION in a 6 L bath of TSB adjusted to pH 7.4 for 24 hours in the coldroom (TSB is Tris saline buffer: tris base 3.075 g, NaCl 6.24 g, HCl 23 mL (IN), add $H_2O$ to 1000 mL. This solution has a pH of 7.2 and an osmolarity of 290 mOsm/L).

The resulting colloidal solution contained iron oxide particles with a particle size of 2.9±1.3 nanometers. 95% of the particles were smaller than 5 nanometers, as measured by electron microscopy. The solution can be stored for prolonged periods of time. Lyophilization is the preferred form of storage. It does not alter the magnetic behavior of the monocrystalline particles.

When used alone (i.e. in the absence of a specific affinity substituent), the agents are useful in imaging lymphatic, bone marrow, splenic, and hepatic tissue. Suitable dosages range from 0.1 mg/kg/day to 20 mg/kg/day. Following administration (e.g., intravenous, intraarterial, subcutaneous, intramuscular, intraparenchymal, intracavity, topical, ocular, oral or rectal administration, with intravenous injection being preferred), NMR imaging (e.g., spin echo, gradient echo, fast imaging, echo planar, or susceptibility imaging) is carried out; the choice of pulse sequence (inversion recovery, IR; spin echo, SE) and the values of the imaging parameters (echo time, TE; inversion time, TI; repetition time, TR) will be governed by the diagnostic information sought.

Similar dosages and imaging parameters are used where the particles are coupled to specific affinity substituents. Examples of specific in vivo imaging procedures are described below.

The iron oxide monocrystalline particles can be used as is (see above) or labelled to specific affinity labels if targeting is desired by mixing the particles with a solution of the label, followed by sonification. Covalent chelating agents are not used. To maximize biological activity of the label, labelling is not performed until immediately prior to administration.

Examples of specific labelling procedures are described below.

EXAMPLE 2

This example describes the preparation of monocrystalline iron oxide particles coupled to antimyosin.

0.3 mg of cardiac myosin F(ab')$_2$ fragment were reacted with 1 mg of iron oxide monocrystalline particles prepared as described above. Reaction was accomplished by sonication of the mixed solution in an ice water bath at 30 W with 1 second intervals for 10 seconds (3 cycles).

Figure 5:
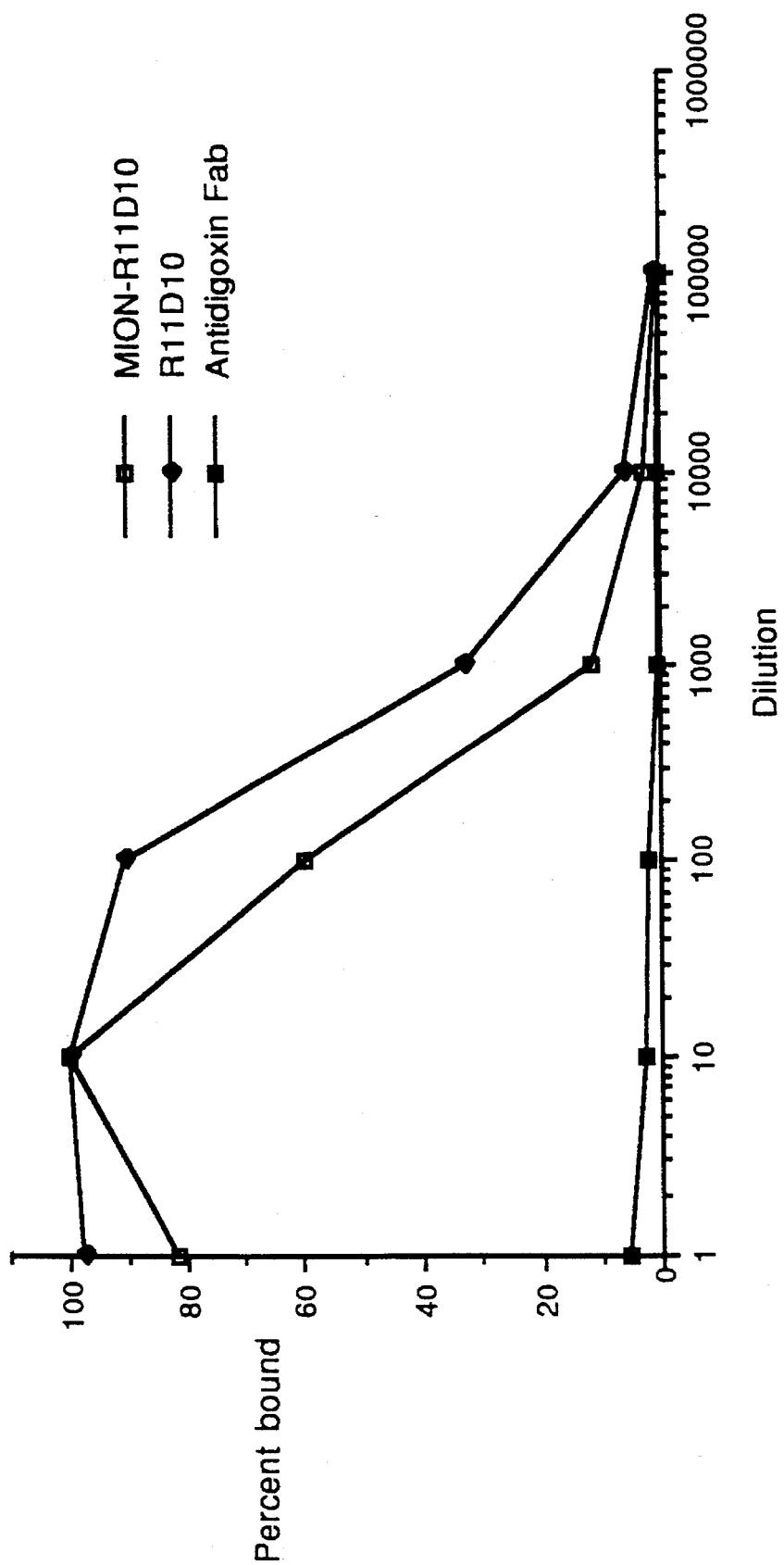
FIG. 5 is a plot of percentage bound by dilution illustrating retained binding affinity for human heart myosin.

The quality of the noncovalent binding was assessed using standard affinity column chromatography and radioimmunoassay (RIA). For column chromatography, the particles were reacted with $^{111}$In-labelled antimyosin, and the resulting product fractionated through a Sephadex column in 0.9% NaCl to which 0.002% sodium azide had been added. Radioimmunoassay was carried out using a non-specific antibody as a normal control. The results demonstrated that nearly all the antibody was tightly attached to the particles. (FIG. 5)

The above-described procedure was also used to prepare iron oxide particles coupled to asialofetuin and to human IgG. Coupling of wheat germ agglutin (WGA) to the iron oxide particles was carried out by dissolving 0.2 mg of peroxidase-labelled WGA (Sigma Chemical Co., St. Louis, Mo.) in 2 ml of a solution containing 80 μmol/ml of the iron oxide particles, followed by sonication in an ice water bath at 30 W with 1 second intervals for 10 seconds (3 cycles).

EXAMPLE 3

This example describes the preparation of monocrystalline iron oxide particles labelled with monocytes. MION are "stored" within the monocytes, providing a useful means of increasing delivery of the particles, e.g., to the lymph nodes. Because the monocyte surface is not modified, the labelled monocytes are not recognized as foreign cells by the immune system.

Monocytes in minimal essential medium (MEM) with 10% fetal calf serum and EDTA in phosphate buffered saline (PBS) were obtained from rodent whole blood. The monocytes were then incubated with monocrystalline iron oxide particles prepared as in Example 1 (200 mol Fe/ml) at 37° C. in $CO_2$ atmosphere for 2 hours. The cell culture was then centrifuged and the monocytes washed three times in fresh MEM-10% fetal calf serum/EDTA solution. Cell viability was assessed by tryan blue staining and cell density was adjusted by diluting the suspension with normal saline immediately before injection.

Histologic studies demonstrated that large stainable amounts of monocrystalline iron oxide particles were taken up by the monocytes. Cytologic studies did not reveal any toxic effects on cell viability.

In addition to monocytes, red blood cells, white blood cells, and lymphocytes may be used.

EXAMPLE 4

Myocardial infarcts were visualized as follows.

200 μmol Fe/kg of monocrystalline iron oxide particles coupled to antimyosin prepared in Example 3 were administered intravenously to animals which had sustained a myocardial infarct prior to administration. The infarct was produced by temporary ligation of the left anterior descending coronary artery. Magnetic resonance (MR) imaging was performed 1–2 hours following the single intravenous injection of contrast agent.

The infarct in the territory of the artery was not clearly visible before administration of the contrast agent. Following administration, however, the infarcted heart muscle showed considerable uptake of the contrast agent, resulting in visible MR signal decrease and increased contrast, as shown in FIG. 14. As a result, the entire infarct could be readily seen. Specificity of uptake was corroborated by scintigraphy of radioactively labelled agent and histopathology, including iron staining, FITC-labelling, and control experiments.

EXAMPLE 5

Asialoglycoprotein receptors on hepatocytes were visualized as follows.

In a first experiment, rat liver relaxation times were measured a) prior to administration of contrast agent, b) after intravenous administration (>3 half lifes) of 10 μmol of iron oxide particles coupled to asialofetuin (ASF) prepared in Example 2 (positive control) and c) after intravenous administration (>3 half lifes) of 10 μmol of the monocrystalline iron oxide particles alone (negative control) (n=3 rats in each group). The following $T_2$ relaxation times were obtained:

No contrast agent: 39.7±1.2 msec

MION: 23.5±1.1 msec

MION-ASF: 20.0±0.5 msec

The lower $T_2$ value of the monocrystalline iron oxide-ASF particles indicates specific uptake by the asialoglycoprotein receptor system of the hepatocytes.

Figure 1:
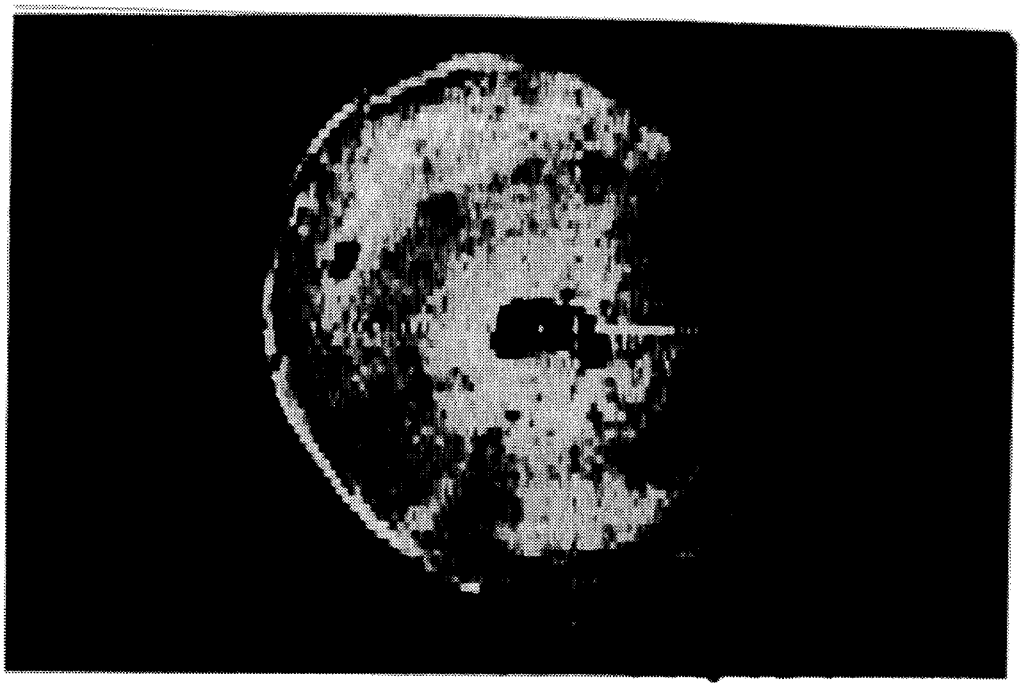
FIG. 1 is an NMR image of infarcted heart muscle (rat) following intravenous administration of contrast agent (MION-$R_{11}D_{10}$).
Figure 2:
FIG. 2 is an in vivo NMR image obtained after administration of contrast agent (MION-ASF) targeted to hepatic asialoglycoprotein receptors.

In a second experiment, MR imaging was performed in live animals and receptor images were obtained. The results demonstrated significant decrease in liver signal intensity after intravenous administration of the iron oxide-ASF contrast agent. Pre- and post-contrast images (shown in FIG. 2) reflect the in vivo distribution of hepatic asialoglycoprotein receptors. Histology confirmed the presence of stainable iron within the hepatocytes.

EXAMPLE 6

Visualization of inflammatory tissue was carried out as follows.

200 μmol Fe/kg of monocrystalline iron oxide particles coupled to human IgG prepared in Example 2 were administered intravenously to animals which had sustained an inflammation in the left hind leg prior to administration. The inflammation was produced by intramuscular injection of bacterial toxin. Eight hours following the injections MR imaging was performed.

As shown in FIG. 13, the site of inflammation was visible by MR as an area of nonspecifically slightly increased MR signal intensity on $T_2$ weighted spin echo pulse sequences (due to edema). Following administration of the agent, the inflamed tissue showed considerable uptake of the directed iron oxide-IgG contrast agent, resulting in visible MR signal decrease. Consequently, the site of inflammation could be clearly identified. When the iron oxide particles alone were injected, there was no uptake at the site of inflammation, demonstrating the specificity of the targeting approach. Specificity of uptake was also corroborated by scintigraphy of radioactively labelled agent and histology.

EXAMPLE 7

4 μl of monocrystalline iron oxide particles coupled to WGA lectin prepared in Example 3 were administered into the posterior chamber of rodent eyes by neuromicrosurgery. MR imaging was then performed 2 hours and 2 days following the injections. The results demonstrated uptake of the WGA-labelled monocrystalline iron particles into the optic nerve with subsequent deposition on the optical cortex.[1]

[1] MION-WGA was also administered to the sciatic nerve and perinerval tissue (FIG. 12). MR imaging showed a decrease in nerve signal intensity which histologically corresponded to axonal transport of the contrast agent.

For example, in addition to NMR imaging, the agents can be used for in vitro studies of, e.g., cell receptor systems, cell surfaces, or subcellular structure (e.g., mitochondria, endoplasmic reticulum, cell nuclei, etc.) using techniques such as autoradiography, histology, electron microscopy, blotting immunodetection, and NMR microscopy. In the case of autoradiography, the particles are radioactively labelled, e.g., with $^{59}$Fe. Because the particles are electron dense, they are easily seen on electron micrographs. They can also be stained with, e.g., iron stains in histologic sections.

The following example describes the use of iron oxide monocrystalline particles as a specific staining agent for histology.

EXAMPLE 8

Monocrystalline iron oxide particles coupled to antimyosin were prepared as described in Example 3. Rodent heart muscle was cryosectioned (7 μm sections) and dried on microscopic slides for 20 minutes at 37° C. Following drying, the sections were incubated with antimyosin-labelled monocrystalline iron oxide particles for one minute, after which the sections were counterstained with iron Prussian blue stain. Specific uptake of the contrast agent into myosin-containing muscle fibers was demonstrated by histology. Thus, the labelled monocrystalline iron oxide particles can be used as an ultrasmall iron probe targetable to a variety of cell-specific markers. Because of the small size of the particles, native cell morphology is maintained and transcytosis is increased.

Prefered MION synthesis

EXAMPLE 9

This is a procedure to obtain monocrystalline iron oxide crystals at a higher yield and with a higher relativity than as described under "MION synthesis".

1. Dissolve 13.5 g FeCl3 6H2O ($Fe^{2+}$/$Fe^{3+}$ratio=2:1) and 28.2 g dextran (MW9,400) in 300 ml of water (Fe/dextran ratio=50:1). Another preferred method uses higher concentrations of dextran (up to 70%). The high viscosity favors the formation of MION. In addition, the yield of MION is increased at higher dextran concentrations. Excessive surface bound dextran can later be removed from particles by mild hydrolysis (pH of 15) or enzymes (e.g., dextranase). In another preferred method dextran in this step can be substituted by modified dextrans e.g., aminated dextran, thiolated dextran, dextrans with aldehyde or carboxylic acids etc.

2. Prepare 2N NaOH and slowly increase the pH to 7–12 (pH of 9–11 are preferred). The addition should be undertaken dropwise and take approximately 2 hours. Temperature is low (1°–30° C.; preferably 5°–10° C.); continuous stirring. First a brown flocculation (polymer I) and later a dark green dispersion form (polymer II) form. Initial slow pH raise is very important and determines how much and which kind of iron oxide will be formed.

3. Heat the dark green solution to 90° C. for 15 minutes. During this procedure the green solution turns black-brown indicating oxidation of polymer II to magnetite type iron oxide.

4. Cool the solution to 4° C. and readjust the pH to 7.0–8.0. This step is very important and ultimately determines the yield of MION. If the pH is not readjusted, polycrystalline particles will form.

5. Sonicate the solution in an ice bath using a continuous pulse at miximum power (usually 40–80 W) for 30 minutes. Readjust hte pH to 7 (important step). This step #5 is optional.

6. In another preferred embodiment rapid dehydration of particles with ethanol (or other organic solvents) is performed. Rapid dehydration of the particle surface precipitates iron oxides and allows separation from nonrecated contaminants; this step also results in more homogenous monocrystaslline iron oxide preparation and also increases the yield of monocrystalline particles. The ethanol precipitated iron oxide can be easily resolubilized in water.

7. Centrifuge the sample at 25,000 RPM for 30 minutes (or equivalent at lower RPM). The sample is now ready for column fractionation, reverse osmosis or ultrafiltration to remove polycrystalline particles. Columns separation can be done in sepharose CL4B with water or TSB as an eluent (TSB is Tris saline buffer: tris base 3.075 g, NaCl 6.24 g, HCl 23 mL (1N), add $H_2O$ to 1000 mL. This solution has a pH of 7.2 and an osmolarity of 290 mOsm/L).

10. Dialyze the pooled fractions in a 6 L bath of TSB adjusted to pH 7.4 for 24 hours at 4° C. Alternative solutions are physiologic saline, Ringer-lactate or physiologic dextrose solutions. Adjustment of the osmolarity is important before injections of the hypotonic solution is performed. Alternative methods of dialysis include ultrafiltration with appropriate filters, osmosis and reverse osmosis.

11. Readjust the osmolarity with concentrated salts (e.g., NaCl) or sugars. The solution is now ready for injection or lyophilization.

Several modifications of the above procedure are possible:

1. Reducing substances in step one can be used to prevent premature oxidation of Fe2+ to $Fe^{3+}$ before the reaction occurs. Preferred reducing agents are ascorbic acid, borohydrate, cyanoborohydrides, hydroxyanisole, hydroxyloluene, hypophosphorous acid, monothioglycerol, proply-gallate, tannic acid, sodium formaldehyde sulfoxylate, sodium metabisulfite, sodium thiosulphate, sulphur dioxide, tocopherol and excipients. Alternatively, the reaction can be performed under nitrogen (use deoxygenized water). A third possibility is to perform the reaction in excess of Fe2+ (Fe2+/Fe3+ ratio>2:1).

2. Alternatively, the reaction can be started entirety from Fe2+ (without Fe3+) in the presence of a controlled amount of oxidants including $O_2$, $KlO_3$, $Na_2SO_3$, $NalO_4$, etc.

3. Iron salts other than halides may be used for the synthesis. Possibilities include organic salts and water soluble inorganic salts.

4. Dextran preferably is of low molecular weight type to reduce the risk of anaphylactoid side reactions. Preferred dextrans have a MW of 2,000 to 5,000.

5. Inorganic phosphate and nitrate may improve the controlled growth of magnetite crystals. Less than 10% $PO_4^{-3}$ enhances crystall morphology whereas –15% inhibits crystal formation. The magnetite crystals have octahedral surfaces with smooth {111} faces.

The physical characteristics of the new MION preparation are:

R2 relaxivity 110.7 $(mM\ sec)^{-1}$ (range 5–200)

R1 relaxivity 22.3 $(mM\ sec)^{-1}$ (range 2–50)

Induced magnetization at 1.5 T 63.8 emu/g Fe size of iron oxide core by EM 4.3±1.1 nm crystal morphology (high res EM) monocrystalline octahedral Moesbauer spectroscopy K=0.8×10$^6$ ergs/cm$^3$, corresponding size: <6nM HPLC monodisperse, single peak suspension (in contrast to multiple peak suspensions as in AMI-patients). This and size analysis by EM/hysteresis are convincing evidence of monocrystallinity Hysteresis plot A magnetization plot demonstrates superparamagnetic behavior of MION. At 1.5 T the induced magnetization is 63.8 emu/g Fe (293 K). There is no remanence at OT. Further, a graph of M (emu/g Fe) vs Field Strength (KG) shows a much steeper rise in magnetization using the preferred synthesis method compared to the two step process. For example, at 5 KG, the two step process provides induced magnetization of about 15 emu/g Fe, whereas the preferred method provides a magnetization of about 55 emu/g Fe. At 10 KG, the 2 values are about 25 and 60 emu/g Fe, respectively.

Size distribution

EM shows a unimodal peak. The mean diameter of the iron core of MION is 4.3 nm. 95% of MION are smaller than 5 nm and none are larger than 8 nm.

PION Synthesis

EXAMPLE 10

Firm attachment of a synthetic compound (ASM grafting) to MRC during synthesis may be achieved. The reaction steps are similar as for preferred MION except for the first step; occasionally additional steps are required to remove unreacted synthetic compounds. PION can be monocrystalline or polycrystalline. PION differ from other polycrystalline iron oxide preparations in their unique ASM coating. Preferably, the solutions contain aggregates of individual crystals. The following procedure produces MRC to which are attached polysorbates (polyoxyethylene derivatives of sorbitan esters):

1. Dissolve 13.5 g FeCl3.6H2O, 20.0 g FeCl2. 4H2O ($Fe^2+/Fe_3+$ ratio=2:1) and 100 ml of polyoxyethylene derivatives of fatty acid sorbitan ester (Tween 20) in 300 ml of water.

2. Prepare 1N NaOH and slowly increase the pH to 8 (approx. 280 ml of NaOH are needed). The addition should be undertaken dropwise and take approximately 2 hours. Temperature is 25° C.; continuous stirring. First, a brown flocculation (polymer I) and later a dark green dispersion forms (polymer II).

3. Heat the dark green solution to 90° C. for 15 minutes. During this procedure the green solution turns black/brown indicating oxidation of polymer II to magnetite type iron oxide.

4. Cool the solution to 4° C. and readjust the pH to 7.0 with HCl 5N.

5. Sonicate the solution in an ice bath using a continuous pulse at maximum power (usually 40–80 W) for 30 minutes.
6. Readjust the pH to 7.
7. Centrifuge the sample at 13,000 RPM for 1 hour. Pass the supernatant through a 0.2 m filter (e.g., Gelman, Acrodisk). The sample is now ready for dialysis in TSB adjusted to pH 7.4. Alternative solutions are physiologic saline. Ringer-lactate or physiologic dextrose solutions.
8. Concentrate and wash the dialyzed MION fraction using an AMICON cell. Readjust the osmolarity with concentrated salts (e.g., NaCl) or sugars. The solution is now ready for injection or lyophilization.

Several modifications of the above procedure are possible.

1. Reducing substances in step one can be used to prevent premature oxidation of $Fe^{2+}$ to $Fe^{3+}$ before the reaction occurs. Preferred reducing agents are ascorbic acid, borohydrate, cyanoborohydrides and tannic acid. Alternatively, the reaction can be performed under nitrogen (use deoxygenized water). A third possibility is to perform the reaction in excess of $Fe^{2+}$ ($Fe^{2+}/Fe^{3+}$ ratio >2:1).
2. Alternatively, the reaction can be started entirely from $Fe^{2+}$ (without $Fe^{3+}$) in the presence of a controlled amount of oxidants including $O_2$, $KIO_3$, $Na_2SO_3$, $NaIO_4$, etc.
3. Iron salts other than halides may be used for the synthesis. Possibilities include organic salts and water soluble inorganic salts.
4. Other synthetic ASM which have been used in step 1 of the PION synthesis are listed above.
5. Fractionation is not necessary unless monocrystalline or oligocrystalline particles are desired.
6. Inorganic phosphate and nitrate may improve the controlled growth of magnetite crystals. Less than 10% $PO_4^{3-}$ enhances crystal morphology whereas >15% inhibits crystal formation. The magnetite crystals have octahedral surfaces with smooth {111} faces.

Figure 4:
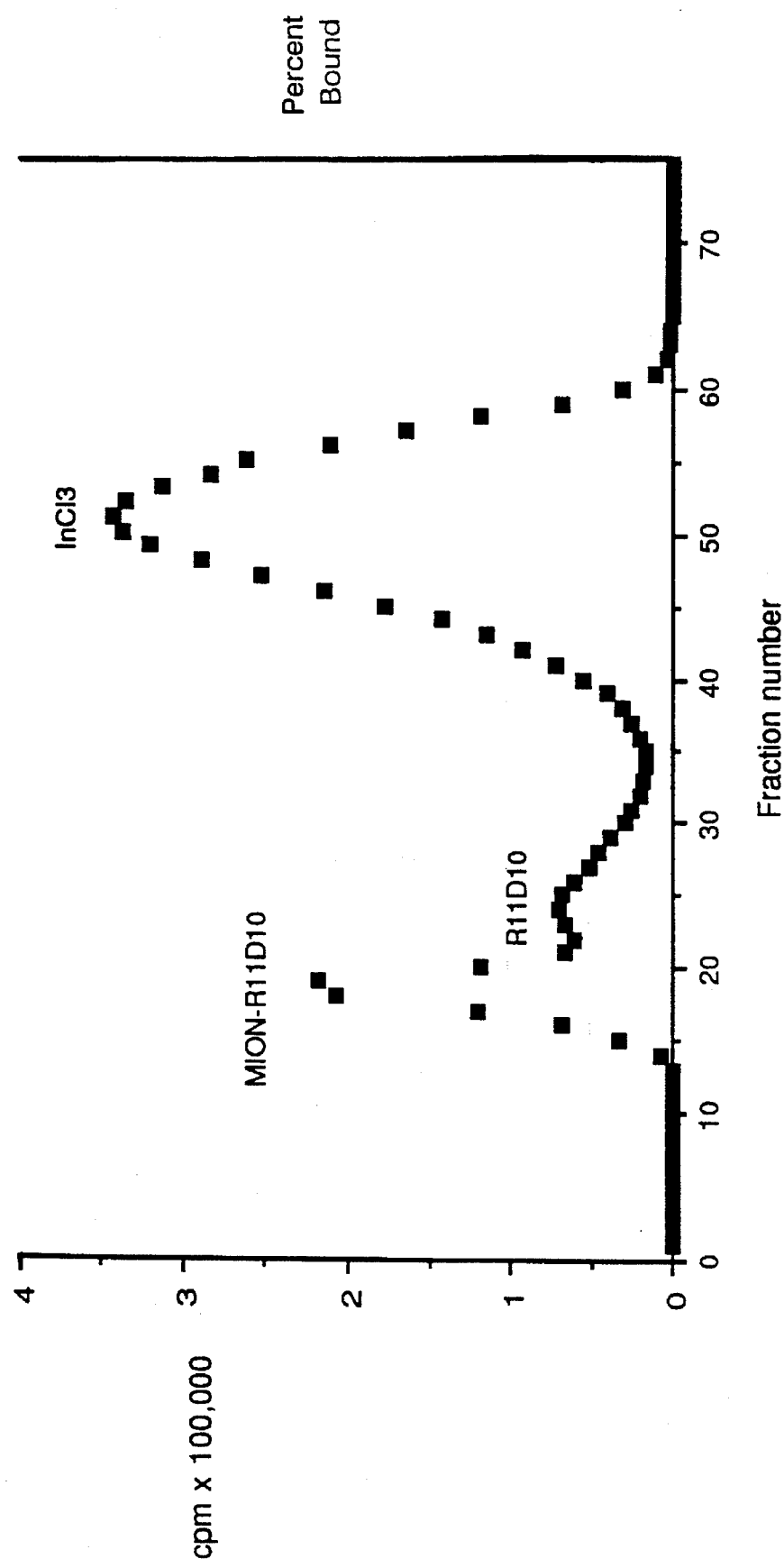

The above synthetic methods can be used in either batch or continuous production of MION and other MRC-ASM. Continuous synthesis has the advantage of producing identical compositions over time and can be scaled up for large scale commercial production. FIG. 4 is a diagrammatic illustration of apparatus useful in the continuous production method. Tanks 10 and 12 store sodium hydroxide and iron chloride/dextran solutions, respectively. These reactants are pumped, via pumps 14 and 16, into reaction chamber 18, where they are allowed to react to form the crude particle suspension. That mixture passes over heating elements 20 for oxidation and final particle formation, and then to sonicator 22. Further purification is carried out in magnetic separation chamber 24, and the final purification step occurs in ultrafiltration chamber 26.

Alternative ferro- and superparamagnetic compounds: Biogenic Iron oxides

Several biologically occurring iron oxide substances have strong magnetic properties and can be used as contrast agents for MR imaging. These agents (including ferritin, hemosiderin, and biogenic magnetite) can be used in either their native form or modified by attachment to TSM. These agents have the advantage of being monodisperse and monocrystalline.

Ferritin

Ferritin is an iron storing protein found in animals, plants and humans. It is characterized by its ability to store iron as a microcrystalline hydrous-ferric oxide-phosphate (ferrihydrate-phosphate) complex enclosed with a protein shell. Each molecule contains approximately 3,000 iron atoms [Treffry, Inorgo Biochem. 1987; 31:1–6] and most ferritins contain phosphorous. The formula of a specific iron core has been described as $(FeOOH)_8(FeO:OPO_3H_2)$ [Michaelis, J. Biol. Chem. 1943; 148: 463].

Ferritin from horse spleen can be commercially obtained (e.g., from Sigma, St. Louis, Mo.) and modified for MR imaging. The modification includes dialysis (24 hours in TSB solution at pH 7.4) to remove low molecular weight contaminants. If desired, modulation of surface groups can be performed to convey target specificity. For example, ferritin can be galactosylated by reaction mechanisms (see below). Galactosylated ferritin has a specificity for the asialoglycoprotein receptor on hepatocytes. In another embodiment, monoclonal antibodies are attached to ferritin using standard chemical linking procedures.

Hemosiderin

Iron oxide cores of hemosiderin have a ferrihydrite structure similar to that of ferritin cores [Dickson, Biochim Biophys. Acta 1988; 957: 81–90]. Crystallographic data indicate a microcrystalline goethite structure. In contrast to ferritin, the polypeptide outer shell in hemosiderin may not form a complete envelope [Dickson, Biochim. Biophys. Acta 1988; 957: 81–90]. The core diameter is 5–7 nm. Hemosiderin can be commercially obtained (e.g., from Sigma St. Louis, Mo.) and modified for MR imaging. The modification includes dialysis (24 hours in TSB solution at pH 7.4) to remove low molecular weight contaminants. If desired, modification of surface groups can be performed to convey target specificity. As with ferritin, hemosiderin can be galactosylated by reaction mechanisms. Galactosylated hemosiderin has a specificity for the asialoglycoprotein receptor on hepatocytes. In another embodiment, monoclonal antibodies are attached to hemosiderin using standard chemical linking procedures.

Biogenic Magnetite

Magnetites have been detected in tissues of species that are known to respond to magnetic fields (fish, birds, bacteria). These compounds have the advantage that they are crystallographically pure, generally with a cubo-octahedral {111} faces. These compounds can be harvested from fish (Sockeye salmon) or bacteria. Particle size range is 25–60 nm [Mann, J. Exp. Biol. 1988; 140: 35–49]. Compounds are purified and modulated as described for ferritin.

Organic polymeric compounds

Organic compounds devoid of iron can be synthesized that exhibit ferro- or superparamagnetic behavior. These compounds can be classified into one of the following groups: (a) compounds with a one-dimensional structure (e.g., polyBIPO; Korshak, Nature 1987; 326: 370), (b) compounds with a two-dimensional structure (e.g., polyradicals based on the graphite structure) and (c) compounds with a 3-dimensional molecular structure (e.g., intermediate diamond-graphite structures; Ovchinnikov, Frontiers of Macromolecular Science, Blackwell Scientific Publication, 1989: 455–461).

Three-dimensional compounds can be used as the magnetically active ingredient for MR contrast agents. These 3-D compounds can be synthesized by polymerization of acetylene and diacetylelen derivatives, by oxidation of traditional polymers with properly situated side groups, and by controlled pyrolysis of some polymers. The preferred technique for synthesis is pyrolytic decomposition (900°–1100°) of polyarylnitrile in a reactor (synthesis first described by Ovchinikov, Dokl Ak Nauk SSR 1988; 302: 889). Such synthetic magnetic particles are monocrystalline.

Polymeric Iron Compounds

Although a variety of paramagnetic ions ($Co^{2+}$, $Cu^{2+}$, $Mn^{2+}$, $Gd^{3+}$, $Dy^{3+}$ etc.) can be attached to biomolecules, $Fe^{3+}$ is the preferable ion for intracellular and macromolecular MR contrast agents. Iron occurs naturally in many cells and is non-toxic.

IqG-(DTPA-Fe)$_n$

Multiple iron chelates can be attached to virtually any protein by the carboxy-carbonic anhydride method [Krejcarek, 1977 #46; Khaw, 1984 #36]. Preferred chelates are diethylenediamine pentaacetic acid (DTPA) and ethylenediamine tetraacetic acid (EDTA) but others are possible. Once the chelate is attached to the protein, transchelation with $Fe^{3+}$ can be performed. The reaction product is a protein with multiple Fe-DTPA side chains.

EXAMPLE 11

Fe-labeled IgG may be synthesized for use as an MR contrast agent. Human, nonspecific, polyclonal, immunoglobulin modified for intravenous use was obtained from Cutter Biological, Inc. (Berkeley, Calif.) and was conjugated with diethylenetriamine pentaacetic acid (DTPA) by the carboxy-carbonic anhydride method. The DTPA coupled IgG was diluted to 5 mg of protein per ml in 0.9% sodium chloride. Prior to column fractionation, IgG-DTPA was labeled with sterile, pyrogen-free $Fe^{3+}$ by citrate transchelation. Chemical purity was determined by eluting the sample through a 10 mL Sephadex G25 column (Pharmacia, Piscataway, N.J.) equilibrated to saline.

Polylysine-(DTPA-Fe)$_n$

DTPA was attached to polylysine, MW 23,000. 30 mg of polylysine were dissolved in 12 ml of 0.1M carbonate buffer at pH 9.1. To this solution 60 mg of cyclic DTPA were added. The DTPA was suspended in 1.6 ml DMSO of (37.5 mg/ml). The reaction product was stirred incubated overnight at 4° C. Finally, the reaction product was dialyzed in 6l dd$H_2O$ to which had been added 19 g Chelex-100/L. The polylysine-(DTPA)$_n$ was then incubated with 0.5 m $FeCl_3$ for 30 minutes and dialysis against dd$H_2O$ was repeated. Finally, the complex was lyophilized and stored for future use.

Other Compounds
Radioactively Labeled MRC

In the following description MRC were synthesized with gamma-emitting radionuclides. The resulting complexes can be used in studies of organ and tissue function (gamma camera, MRI), diagnosis and as magnetic radiotherapeutic agents. Preferred radioisotopes include: $^{111}In$, $^{99m}Tc$, $^{59}Fe$, $^{57}Fe$, $^{55}Fe$, $^{52}Fe$, $^{201}Tl$, $^{67}Ga$, $^{133}Ba$, and $^{137}CS$. Whereas, iron isotopes such as $^{59}Fe$, $^{57}Fe$, $^{55}Fe$, $^{52}Fe$ can be easily substituted during the MION and PION synthesis, other metal isotopes can only be incorporated into the MRC in limited quantities ( "doping") . Trivalent isotopes such as $^{111}In^{3+}$ occupy $Fe^{3+}$ sites in the iron oxide polymer. Although there are common features in the chemistry of the two ions, $^{111}In^{3+}$ is larger than $Fe^{3+}$ (ionic radius is 0.95 for $Fe^{3+}$). $^{111}In$ and 99m$TcO_4$ doped PION are synthesized as follows:

EXAMPLE 12

1. Dissolve 13.5 g $FeCl_3.6H_2O$, 20.0 g $FeCl_2.4H_2O$ ($Fe^{2+}/Fe^{3+}$ ratio=2:1), 100 ml of polyoxyethylene derivatives of fatty acid sorbitan ester (Tween 20) and 5 mCi of radioactive $^{111}In$ or $^{99m}TcO_4$ in 300 ml of water.

2. Steps 2–6 are similar as described in section Example 10.

3. Centrifuge the sample at 13,000 RPM for 1 hour. Discard the radioactive sediment, pass the radioactive supernatant through a 0.2 m filter (e.g., Gelman, Acrodisk), dialyze and concentrate. The solution is now ready for injection or lyophilization.

Substituted iron oxide metallo-complexes

Iron in MRC's can be substituted by other di- and trivalent metals such as Ca, Zn, Cr, Co, Cu etc. This is done by simple addition of soluble salts of the desired metal during step 1 of the synthesis of P-MION or PION (section 3.3). Magnetic susceptibilities in these "substituted MRC's" decrease with an increasing amount of substitution (DeSitter 1977, Ok 1978). For the magnetite type MRC the chemical formula is $M_xFe_{3-x}O_4$, where M is a divalent cation. For more complex iron oxides a representative formula could be ($M_xFe_{3-x}O_4$) a ($N_yFe^{2-y}O_3$) b, where N is a trivalent cation, and M a divalent cation.

Paramagnetic iron oxide compound with attached aminated sugars

Paramagnetic iron complexes can be easily synthesized from $Fe^{3+}$ and aminated sugar solutions to be used as MR contrast agents. The preferred aminated sugar is N-methylglucamine (meglumine).

EXAMPLE 13

1. Dissolve 13.5 g $FeCl3.6H2O$, 20.0 g $FeCl2.4H2O$ ($Fe^{2+}/Fe^{3+}$ ratio=2:1), 15.0 g sodium meglumine in 300 ml of water.

2. Heat the solution to 80° C. and add 10N NaOH until pH 9 g at which the solution turns dark brown and contains polymerized iron oxide products.

3. Centrifuge, dialyze and concentrate as described in Example 10.

Paramagnetic iron oxide with attached carboxylic acid sugars

Paramagnetic iron complexes can be easily synthesized from $Fe^{3+}$ and carboxylic acid sugar solutions to be used as MR contrast agents. The preferred aminated sugars are glucuronic, galacturonic acid and alginic acid (see the following example).

EXAMPLE 14

1. Dissolve 13.5 g $FeCl3.4H2O$, 20.0 g $FeCl2.6H2O$ ($Fe^{2+}/Fe^{3+}$ ratio =2:1), 15.0 g of glucuronic acid, galacturonic acid or alginic acid in 300 ml of water.

2. Heat the solution to 80° C. and add 10N NaOH until pH 9 g at which the solution turns dark brown and contains polymerized iron oxide products.

3. Centrifuge, dialyze and concentrate as described in Example 10. Hysteresis plots of this compounds shows a linear correlation between induced magnetization and applied field strength, a typical feature of paramagnetic compounds.

Covalent attachment of protein type TSM to ASM

This section describes methods for covalent attachment of target specific proteins to hydroxyl, carboxyl or amino groups of ASM.

Aldehyde linkage

It is possible to link proteins, e.g., monoclonal antibodies to MION and PION using hydroxyl groups on the ASM (dextran, polyalcohols, polysorbates etc.). In the binding procedure the ASM hydroxyl group is oxidized to give a functional aldehyde group that can react with amino groups on the antibody molecules. The excess periodate is removed by either dialysis or centrifugation and washing. The product is then incubated with antibody at a suitable pH (5–8) in the dark for 18 hours at 4° C. The linkages are reduced with sodium borohydride to form more stable conditions. This technique can be used to attach secretin, monoclonal antibodies, polyclonal IgG, hexapeptides and WGA lectins to MION, P-MION and PION, using, e.g., the following procedure.

EXAMPLE 15

1. Start out with 1 mg of MION (or PION with hydroxyl groups) to which is added 1 mg of $NaIO_4$. Adjust the pH to 8 with berate if necessary.
2. Wrap the solution in aluminum foil and agitate or nutate for 24 hours in the cold room (4° C.).
3. Wash the solution with 6 mL of $H_2O$. Reconcentrate solution to 1 ml using vacuum dialysis.
4. Add 0.05M borate solution to adjust the pH to 7.5. This solution can be stored at 4° C. but should preferably be rapidly reacted with protein (aldehyde groups are unstable).
5. Use 1 mg Fe and add 1 mg of antibody (best ratio being protein/iron being 1:1).
6. Incubate overnight, then add 1 mg of cyanoborohydride ($KBH_3CN$) per mg of Fe.
7. React for 5–10 hours (4° C.).
8. Solution is ready for chromatography on Sephadex G100. Separate bound and unbound product. Concentrate the labelled complex using an AHICON stir cell.
9. Buffer solution for chromatography: 0.9% NaCl, 0.05M berate, 0.01M citrate (pH 7.5–8.5) .

[2]In another embodiment other techniques of covalent building of TSM to ASM or MRC can be used. These chemical techniques include the carbodiimide method, the cyanogen bromide method, the glutaraldehyde method, the EEDQ method, Woodward's method or SPDP method.

Modification of carbohydrate type ASM

Carbohydrates used as ASM can be modified when chemisorbed to the MRC but are better modified before chemisorption. Attachment of additional sugar residues to polyhydroxyl containing ASM (see Kojima S., Biol Chem Hoppe-Seyler 1990; 372: 331–338) and attachment of amino groups to polyhydroxyl containing ASM can be performed but are not limited to the following reactions:

Carbodiimide mediated coupling of sugar derivatized aliphatic spacer (2.3 epoxypropane)-4-oxybutyric acid Reductive amination in the presage of cyanoborohydrate Diazonium coupling of p-aminophenyl glycosides Conjugation of p-isothiocyanatophenyl glycosides Carbodiimide mediated coupling of p-aminophenyl glycosides Enzymatic attachment of UDP-gal: use of galactosyl transferase UDP-galactose can be attached to proteins or sugars containing N-acetyl-glucosamine residues. This reaction is best performed in the presence of $Mn^{2+}$, at 4° C. and for 20 minutes. The reactions yields Gal-1, 6GlcNac residues on proteins or sugars (Thilo L., Meth Enzymol 1983: 98: 415–421). Galactosyl transferase and UDP-galactose can be commercially obtained (e.g., Sigma Chemicals, St. Louis, Mo.).

Preparation of diaminoethane derivatized dextran

Natural dextran can be derivatized to yield a semi-synthetic aminated dextran derivative. The aminated dextran can be used in the synthesis of PION.

EXAMPLE 16

A dextran solution containing 20 g of dextran (MW 2,000 to 10,000) in 100 mL of 0.05M acetate solution is oxidized with 2.1 g sodium periodate for 2 hours at 23° C. The solution is then dialyzed in 6 l of dd $H_2O$ at 4° C. overnight. The oxidized dextran is mixed with 20 ml of 6M diaminoethane, titrated to pH 8.5. The reaction is stirred at room temperature for 2 hours and quenched with 0.75 g $NaBH_4$. The solution is then dialyzed and ready for further use. Presence of amino groups on the dextran can be determined by the 2, 4, 6-trinitrobenzene sulfonate test.

Modification of natural gums for use as ASM's

A variety of modified complex plant carbohydrates can be used as ASM for the synthesis of MRC-ASM complexes. Unaltered plant gums have the following disadvantages: high molecular weight, possibility of eliciting anaphylactoid reactions, incomplete solubility in water. Partial hydrolysis of these compounds results in smaller carbohydrate units with these advantages:

smaller MW units are less immunogenic;

central galactose groups are exposed;

unwanted surface groups are hydrolyzed (e.g., Nac to $NH_2$.

The following example involves hydrolyzation of gum arabic (obtained from Acacia) resulting in low molecular weight galaclose terminated polysaccharides. This hydrolysis is readily applicable to other gums including gum ghatti and gum traganth. Gums can be obtained commercially. A sample procedure follows:

EXAMPLE 17

1. 20 g of Acacia gum (Sigma Chemicals, St. Louis, Mo.) is dissolved in 100 ml 20% acetic acid or alternatively 5N $H_2SO_4$. The turbid yellow solution is then stirred at 90° C. for 1 hour in a water bath.
2. Neutralize the acidic sugar solution with 10N NaON to quench the hydrolysis. Filter the neutral solution to obtain a clear yellow liquid.
3. Dialyze the sugar solution to remove unwanted salts and low MW sugars (e.g., MW cut-off tubing at MW 2,000).
4. Freeze-dry the dialyzed solution until further use.

Noncovalent Chemisorption of TSM to MRC-ASM

A large variety of hydroxyl, carboxyl, aldehyde, and amine containing TSM can be attached to the MRC-ASM complex by the convenient technology of chemisorption. This interaction is based on van-der Waals forces, ionic bonds and complex formation.

EXAMPLE 18

Electrostatic and complex formation is achieved by reacting 0.3 mg of protein (e.g., IgG) with 1 mg Fe of MRC-ASM (MION or PION type) in a buffer containing 0.145M NaCl and $NaPO_4$ at pH 6.5. Thereafter, sonification is performed in an ice bath (Branson 450 sonifier, Branson Ultrasonics Corp., Danbury Conn.) for three cycles of 5 seconds each. Proteins form bonds with iron oxide hydroxyl groups expressed on the surfaces of iron oxide particles and stabilize these colloids against aggregation.

Receptor agents

ASG receptor

Asialoglycoprotein receptor targeting of iron polymers requires an understanding of the molecular structure of the asialoglycoprotein receptor. The receptor has a high affinity for 3 branched oligosaccharides of which each branch contains a terminal galactose residue. The suprastructure of the receptor has been identified and shown to consist of HL-1 and HL-2 subunits.

The trianntenery sugar with the highest affinity ($7\times10^{-9}$) to the ASG receptor is given by the following chemical formula and the schematic representation:

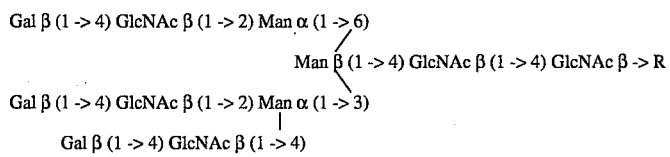
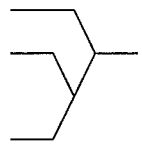

The affinity of different sugar residues to the ASG receptor is given by:

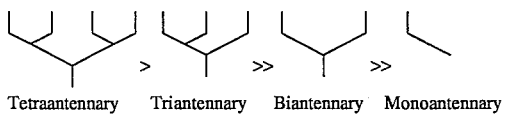

Tetraantennary   Triantennary   Biantennary   Monoantennary

A large variety of galactosylated compounds have an affinity for the ASG receptor. These TSM can be used for drug targeting (Fallon RJ, Schwartz AL, Hepatology 1985:899:901; Trouet A. et al., Nature 1984; 239: 110–112):

| Drug | Carrier |
|---|---|
| Antiviral agents | |
| ARA-AMP | Lactosylated HSA |
| ARA-AMP | Galactosylated Polylysine |
| Trifluorothymidine | Asialofetuin |
| Interferon | Galactosylated derivative |
| Antiparasitic agents | |
| Primaquine | Asialofetuin |
| Antineoplastic agents | |
| Diphteria toxin A | Asialofetuin |
| Dephteria toxin | Asialoorosomucoid |
| Ricin | Asialofetuine |
| Daunorubicine | Galactosylated HSA |
| Diagnostic agents | |
| Tc-99m | Galactosylated HSA |
| Fluorescein | Lactosylated BSA |
| Iron oxide | Arabinogalactan |
| Lipid agents | |
| Cholesterol | Tris-galactose |
| LDL | lactose derivative |
| Antitoxicants | |
| Acetylcysteine | Asialofetuin |
| Folinic acid | Asialofetuin |
| Uridyl monophosphate | Polylysine asialofetuin |
| Proteins | |
| Glucocerebrosidase | Mannosederivative |
| Glucocerebrosidase | Trimannose-dilysine |
| Glutaminase | Asialoorosomucoid |
| tyrosinase | Asialoorosomucoid |
| Immune complexes | Galactosylated Fico II |
| Other | |
| pepstatin | Asialofetuin |
| Iron | Asialotransferrin |
| Bacterial DNA | Asialoorosomucoid/polylysine |

(Meijer DKF et al. Pharm Res 1989; 6:105–118).

Apart from asialoglycoproteins prepared by desialylation of naturally occurring glycoproteins, artificial ligands can also be synthesized in vitro. Neoglycoproteins prepared from albumin can be prepared in large quantities at a relatively low cost. A variety of MRC-ASM preparations were synthesized which exhibit specificity for the asialoglycoprotein receptor on hepatocytes (gal/galNac recognition).

These preparations include MRC-ASM asialofetuin (ASP), MRC-ASM-arabinogalactan (AG), MRC-ASM-galactomannan, MRC-ASM-asialoorodomucoid (ASOR), MRC-ASM-neoglycoalbumins, MRC-ASM-lactoferrin, MRC-ASM-lactosylceramide, MRC-ASM-lactalbumin, and MRC-ASM-galactosylatol dextran.

MRC-ASM-asialofetuin

Asialofeturin can be commercially obtained (Sigma, St. Louis, Mo.). One mg Fe of MRC-ASM (MION or PION type) was reacted with 0.3 mg of asialofetuin using chemisorption. The resulting compound retains its magnetic properties. For one preparation, R2 changed from 5.2 (mM sec)$^{-1}$ for the unlabelled MION to 5.0 (mM sec)$^{-1}$ for MION-ASF. The blood half-life of this compound is less than 15 minutes, a rapid clearance as expected for receptor mediated endocytosis. Efficacy of enhancement of liver signal intensity was proven in an animal model.

MRC-ASM-lactalbumin (and lactoglobulin)

Attachment of lactalbumin and lactoglobulin to P-MION was performed by chemisorption. Both TSM were obtained commercially (Sigma Chemicals, St. Louis, Mo.). When injected IV, the MRC-ASM-lactalbumin compound shows specificity for liver, with a reduction in liver relaxation times and MR signal intensity.

MRC-ASM-lactoferrin

Attachment of lactoferrin to P-MION was performed by chemisorption. Lactoferrin was obtained commercially (Sigma Chemicals, St. Louis, Mo.). When injected IV, the MRC-ASM-lactalbumin compound shows specificity for liver, with a reduction in liver relaxation times and decrease in MR signal intensity.

MRC-arabinogalactan

This complex was synthesized according to the preferred MION process described above, with the modification of using arabinogalactan in step one instead of using dextran. Arabinogalactan is one of the few ASM that at the same time convey target specificity for the ASG receptor. Efficacy in vivo was proven by MR imaging of an animal before and after the IV administration of the compound (FIG. 11).

Arabinogalactans (AG) are highly branched polysaccharides containing frameworks of 1,3 and 1,6 linked -D-galactopyranose residues to which are attached as end groups either single arabinofuranose residues or disaccharide units of 3-0- -L-arabinopyranosyl-L-arabiniofuranose residues. The best characterized AG is that from larch wood, which contains L-arabinose and D-galactose residues in the proportion of 1:6. Similar molecules can be extracted from European larch, Estern larch, and tamarack. AG have a high affinity for the asialoglycoprotein receptor on mammalian hepatocytes (Beuth J, J Cancer Res Clin Oncol 1987; 113: 51–55).

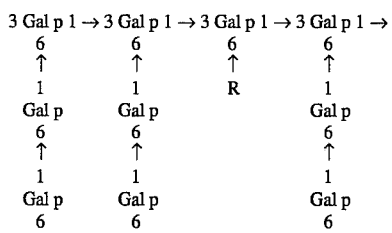

R = Ara f 1.. or Ara p → 3 Ara f 1..

MRC-D-galactomannan

This complex was synthesized according to the MION description with the modification of using D-galactomannan in step 1 instead of dextran. Like arabinogalactan, D-galactomannan is one of the few ASM that at the same time convey target specificity, for the hepatocyte mannose and asialoglycoprotein receptor. Efficacy in vivo was proven by MR imaging of an animal before and after the IV administration of the compound.

A series of closely related galactomannans are found in the seeds of leguminous plants, almost all belonging to the general type formulated in guaran (see chemical structure below). It is likely that different fractions from any one source may differ in the proportions of D-galactose and D-mannose residues. D-galactomannans are readily soluble in water and find commercial use in paper making.

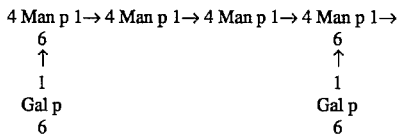

MRC-galactosylated dextran

This complex can be synthesized according to the P-MION or PION description with the modification of using galactosylated dextran in step one instead of using conventional dextran. Like arabinogalactan and D-galactomannan, galactosylated dextran is one of the few ASM's that at the same time convey target specificity for the hepatocyte asialoglycoprotein receptor.

MRC-ASM-neoglycoproteins

MRC-ASM-neoglycoproteins are synthesized as described using MION or PION as starting products. Binding of the neoglycoprotein TSM to a binding site in vivo depends not only on the attached glycoside residue but also on the number of attached sugars, their position on the protein molecule, the method by which they are synthesized, presence of calcium to achieve optimal binding. The preferred neoglycoproteins have more than 40 sugar groups attached per protein. The preferred protein is human serum albumin (HSA). The preferred agents for liver imaging are: MRC-ASM-gal-HSA, MRC-ASM-fuc-HSA, MRC-ASM-man-HSA (p-isothiocyanato glycoside). Efficacy in vivo was proven by MR imaging of an animal before and after the IV administration of MION-gal-HSA and MION-fuc-HSA.

MRC-ASM-asialoorosomucoid

MRC-ASM-asialoorosomucoid can be synthesized as described using MION or PION as starting products. Binding of this asialoglycoprotein conveys specificity of the complex to the asialoglycoprotein receptor on hepatocytes.

MRC-ASM-lactosylceramide

MRC-ASM-lactosylceramide can be synthesized as described using MION or PION as starting products. Binding of lactosylceramide conveys specificity to the asialoglycoprotein receptor on hepatocytes.

Secretin receptor
MRC-ASM-secretin

Attachment of secretin to MION was performed by chemisorption and covalent linkage using the aldehyde method as described above. Secretin was obtained from commercially available sources (Sigma Chemicals, St. Louis, Mo.). An original MION-secretin preparation had an R2 of 6.9 $(mM\ sec)^{-1}$. Efficacy of this compound to modulate pancreas relaxation times and MR signal intensity was proven extensively by in vitro and in vivo assays.

MRC-ASM-cholecystokinin

Attachment of cholecystokinin to P-MION and PION was performed by chemisorption and covalent attachment as discussed above. Cholecystokinin (CCK) was obtained commercially (Sigma Chemicals, St. Louis, Mo.). An original P-MION-cholecystokinin preparation had a R2 of 90 $(mM\ sec)^{-1}$. Efficacy of this compound to modulate pancreas relaxation times and MR signal intensity was proven extensively by in vitro and in vivo assays.

Transferrin receptor
MRC-ASM-transferrin

Hepatocytes display receptors for transferrin (Neutra MR, et al., J Biochem. Histochem. 1985; 33: 1134–1144; Lamparelli RDV et al., Br. J. Haematol. 1989; 72: 100–105). Transferrin is internalized into the cell by receptor mediated endocytosis and the receptor after relinquishing the label is returned to the cell surface as intact apotransferrin. There are between 25,000 and 162,000 receptors on each hepatocyte (Morgan EH et al., Biochem. J. 1986; 237: 163–173). When injected by IV greater than 90% of transferrin is removed by the liver. Only placenta and erythroid marrow have a higher transferrin uptake.

MRC-ASM-transferrin is a MR contrast agent with specificity to hepatocytes and primary liver tumors, both tissues expressing transferrin receptor activity (Sciot R et al., Histopathol. 1990; 16: 59–62). Attachment of transferrin to P-MION and PION was performed by chemisorption. Transferrin was obtained commercially (Sigma Chemicals, St. Louis, Mo.). Efficacy of this compound to modulate liver relaxation times was proven by in vitro and in vivo assays.

Other receptors
MRC-mannan

This complex was synthesized according to the MION description with the modification of using mannan in step 1 instead of using dextran. Mannan was obtained commercially. Mannan is one of the few ASM that convey target specificity of the MRC-ASM complex to hepatocytes and hepatic endothelial cells. R2 relativity of different MRC-mannans varied from 3.4 to 120 $(mM\ sec)^{-1}$. Efficacy in vivo was proven by relaxation time measurements and MR imaging of an animal before and after the IV administration of the compound.

MRC-fucoidan

Fucoidan is a sulphated fucan and contains only L-fucose and 33% sulphate. It comprises 1,2 and 1,4 linked a-fucopyranosyl units with sulphate groups attached to the C3 and C4 of the sugar residues. The MRC-fucoidan complex was synthesized according to the P-MION and PION description with the modification of using fucoidan in step 1 instead of using dextran. Fucoidan was obtained commercially. Fucoidan like mannan is one of the few ASM that convey target specificity of the MRC complex to fucose receptors on hepatocytes. R2 relaxivity of different MRC-fucoidans varied form 1.8 to 120 $(mMsec)^{-1}$. Efficacy in vivo was proven by relaxation time measurements and MR imaging of an animal before and after the IV administration of the compound.

MRC-chitosan

Chitosan is the partly de-acetylated product of chitin, an insoluble polysaccharide from crustacean shell. Chitosan is soluble in weak acids (acetic, formic, malic etc). An MRC-chitosan complex was synthesized according to the MION and PION description above with the modification of using chitosan in step 1 instead of using dextran. Chitosan was obtained commercially, solubilized in acetic acid and acetone, partially hydrolyzed and then freeze dried for further use. R2 relativity of different MRC-chitosans varied from 2.2 to greater than 100 $(mMsec)^{-1}$. Efficacy in vivo was proven by relaxation time measurements and MR imaging of an animal before and after the IV administration of the compound. The MION-chitosan and PION-chitosan complexes are different from the receptor mediated magnetic carriers designed for local drug therapy (Gallo JM, Pharm 1988: 300–304).

MRC-glucomannan

Glucomannans are present in the seeds and bulbs of various land plants, in close association with cellulose in coniferous woods, and to a lesser extend in some hardwoods. Glucomannans are essentially linear polysaccharides that contain 1,4 linked -D-glucopyranose and -D-mannopyranose residues in proportions varying between 1:1 and 1:4:

4 Man p 1 4 Glc p 1 4 Man p 1 4 Man p 1

The MRC-glucomannan complex was synthesized according to the P-MION and PION description with the modification of using gucomannan in step one instead of using dextran. Glucomannan was obtained commercially. Efficacy in vivo was proven by relaxation time measurements and MR imaging of an animal before and after the IV administration of the compound. Glucomannans are recognized by mannose receptors on hepatocytes.

MRC-ASM-lipoprotein (HDL)

There is a high affinity recognition site for HDL on parenchymal, liver endothelial and Kupffer cells (Schouten D et al., Biochem J 1988; 256: 615–621). HDL is expected to deliver cholesterol from peripheral cells, including endothelial and Kupffer cells, to the liver hepatocytes, where cholesterol can be converted into bile acids and thereby irreversibly removed from the circulation. HDL can be easily replaced by -VLDL which shows a higher liver uptake (45% at 10 min). HDL can be obtained commercially (Sigma, St. Louis, Mo.) and reacted to CIP-MION or PION by chemisorption.

MRC-ASM-lipoprotein (LDL).

MRC-ASM-LDL was designed to be targeted to the scavenger receptor on foam cells in atherosclerotic plaques. The structure and function of this scavenger receptor has been recently described [Kodama T, Nature 1990; 343: 531–535]. The receptor has a high specificity for particles with negative charge, maleated BSA, oxidized acetylated LDL and lipophilic antioxidants. Targeting atheromatous plaques allows a) quantitating atherosclerosis, b) studying foam cell formation, c) following a single plaque over time.

Acetylated LDL was commercially obtained and attached to PION using chemisorption techniques. Efficacy of this targeting approach was proven by uptake of PION-acLDL in atheromatous foam cell uptake in an in vitro assay.

Immunospecific agents

MRC-ASM-antimyosin monoclonal Fab (R11D10)

The ability to attach MION and PION to monoclonal antibody was demonstrated by Sephadex G100 column chromatography as illustrated in FIG. 5. Approximately 2 Fab fragments were tightly attached to each MION by reacting 0.3 mg of $R_{11}D_{10}$ antimyosin antibody (Fab) with 1 mg Fe of MION or PION. Binding of Fab to surface bound hydroxyl groups was achieved noncovalently by complex formation and covalently by the potassium periodate method with subsequent borohydride reduction.

Apparent affinity of the MION-attached Fab was determined by solid phase radioimmunoassay. As shown in FIG. 5a, the test sample shows retained binding affinity for human heart myosin over dilution ranges similar to those seen with the positive control sample. These results demonstrate that the coupling of Fab antimyosin does not negatively affect the antigen-binding affinity of the monoclonal antibody. Full antibody reactivity for cardiac myosin is retained, thus producing a biologically active superparamagnetic compound.

High resolution microscopic MR images of infarcted rodent hearts showed that following the administration of MION-Fab, the infarcted region is clearly outlined by the low signal intensity region resulting from site-specific localization of MION-Fab. MR signal intensity on the T2-weighted (TR of 6000 ms; TE of 20 ms; 2 excitations) spin echo image decreased from 119.1±5.8 ms to 19.1±7.6 ms as a result of shortening of T2 by the susceptibility effect of the iron oxide. The infarct size as delineated by MR images correlated well with infarct size as determined by TTC stain. These experiments indicate that the accumulated concentration of targeted agent is sufficiently high to detect infarcted myocardium by immunospecific MR imaging with MION-Fab. Administration of unlabelled MION failed to demonstrate susceptibility changes in infarcted heart, thus indicating that there is no attachment of free MION to areas of infarcted heart.

Results with the antimyosin antibody, and polyclonal IgG indicate that virtually any antibody can be attached to the MRC-ASM complex using the described technology, including Fab, (Fab'), Fc, and MAb fragments.

MRC-ASM-IqG

Polyclonal IgG has been used intravenously in patients, with specificity to sites of inflammation. Polyclonal IgG used as an immunospecific label has the advantage of being readily available as an IV preparation, can be administered in gram quantities, and is much less expensive than immunospecific Fab fragments derived from IgG. The precise mechanisms of localization of non-specific IgG at sites of inflammation are not fully understood.

Figure 6:
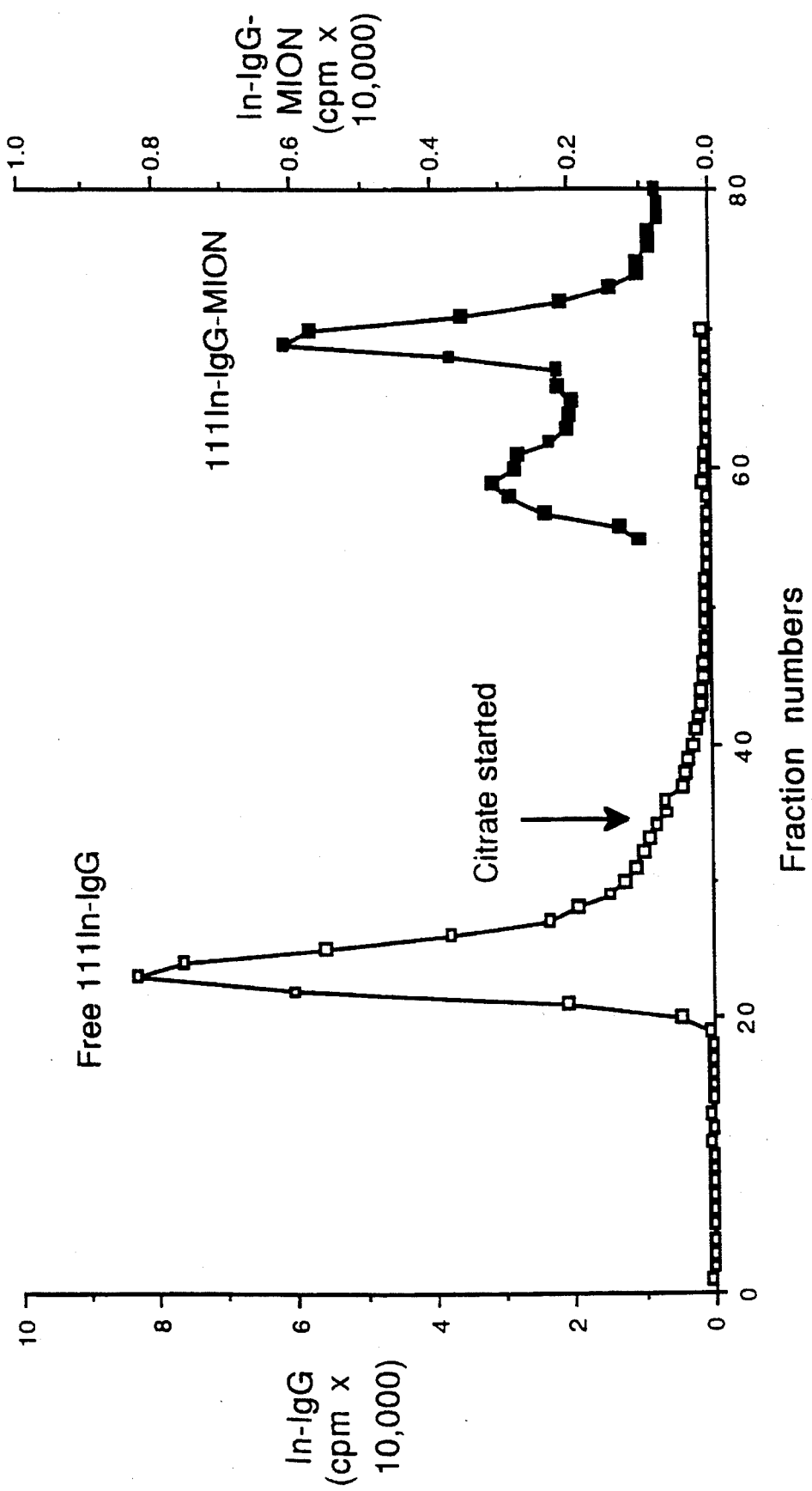
FIG. 6 is a chromatography plot demonstrating attachment of IgG to MRC-ASM.

IgG was attached to P-MION, MION and PION using chemisorption and covalent coupling with the aldehyde method. These contrast agent were designed to improve detection of inflammation, tumor related inflammation and sites of infection. The MION-IgG complex had a molecular weight of 150–180 kDa and an R2 of 7.7–120 $(mMsec)^{-1}$. The blood half-life of this compound was 62 min and the preferred biodistribution in rats was liver> spleen> bone marrow. Attachment of IgG to MRC-ASM was proven by DEAE column chromatography as illustrated in FIG. 6. In vivo efficacy was proven by demonstrating localization of the agent using scintigraphy, MR imaging, and histologic techniques.

Other agents

MRC-ASM-oligopeptides.

Figure 7:
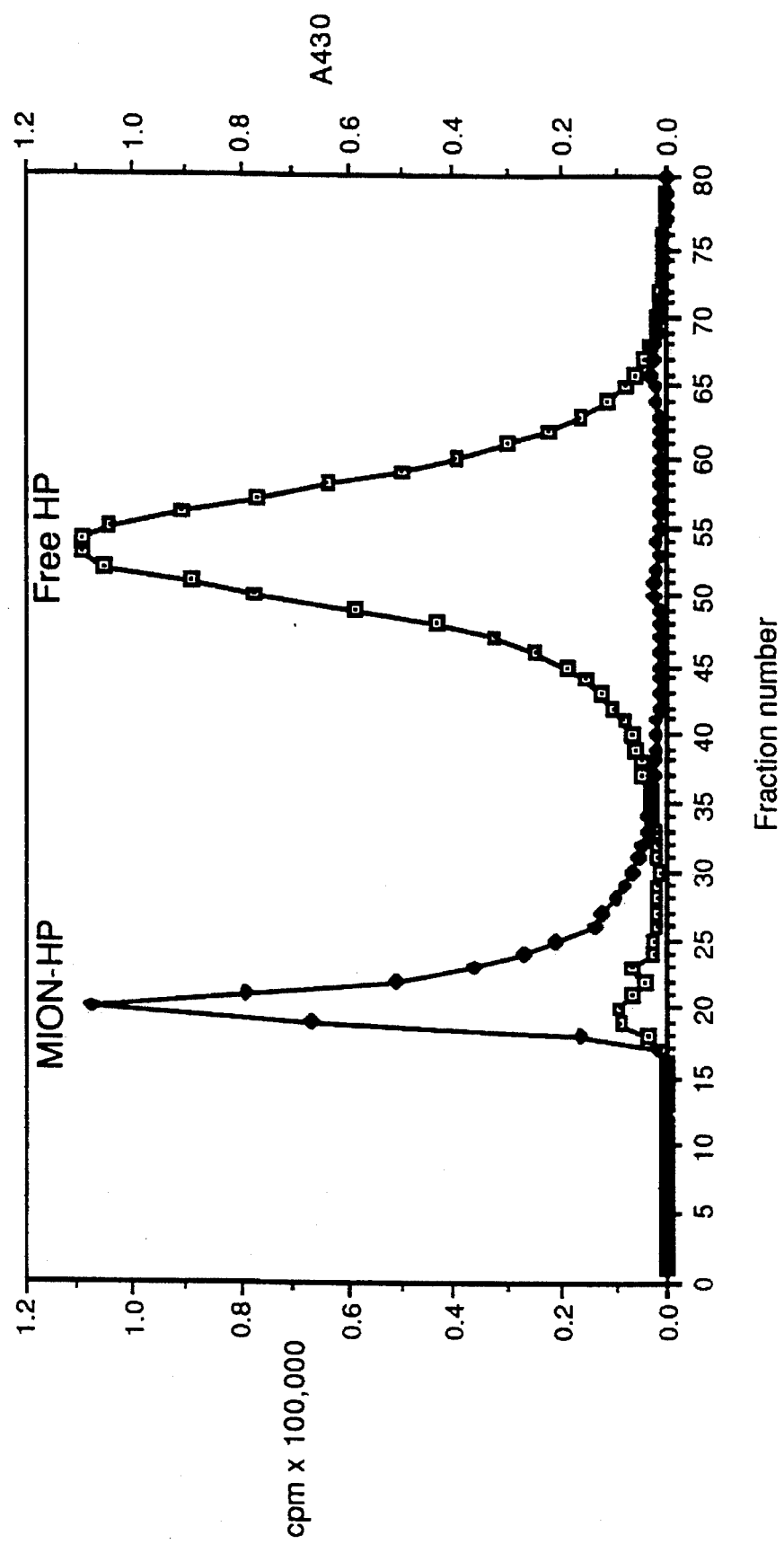
FIG. 7 is a chromatography plot demonstrating attachment of an oligopeptide to MRC-ASM.

This class of contrast agent was designed to enhance detection of sites of inflammation. The chemoattractive hexapeptide (N-formyl-NLE-LEU-PHE-NLE-TYR-LYS), known to localize at sites of inflammation was attached to MION by chemisorption and covalent coupling using the aldehyde method. Attachment was proven by column chromotography, as illustrated in FIG. 7. The hexapeptide was commercially obtained (Sigma Chemicals, St. Louis, Mo.).

R2 of MRC-ASM-hexapeptides ranged form 10 to 150 $(mMsec)^{-1}$. Chemoattraction of the MRC-ASM-hexapeptide complex to leukocytes was demonstrated in an in vitro assay. Efficacy of the compound to change MR signal intensity at the site of inflammation was shown in vivo in an animal model.

Results with this chemoattractive hexapeptide can be extrapolated to a large variety of other bioactive peptides including: adrenocorticotropic hormone and fragments, angiotensin and related compounds, bradykinin and related peptides, chemolactic peptides, hynorphin and related peptides, endorphins and -lipotropin fragments, enkephalin and related peptides, enzyme inhibitors, gastrointestinal peptides, growth hormone releasing peptides, luteinizing hormone releasing hormone and related peptides, melanocyte stimulating hormone and related peptides, neurotensin and related peptides, opioid peptides, oxytoxin, vasopressin, vasotocin and related peptides, parathyroid hormone and related fragments, somatostatin and related peptides, substance P and related peptides.

MRC-ASM-WGA

Wheat germ agglutinin lectin was obtained commercially (Sigma, St. Louis, Mo.). One mg of Fe of MRC-ASM (MION or PION type) was reacted with 0.3 mg of the lectin using chemisorption technology. Efficacy of this agent in enhancing the signal intensity of neurological tissues was proven in several animal models. The compound was injected into the sciatic nerve, intraocularly and into the frontal lobe of rats. MR images demonstrated decreases in signal intensity along nerve tracts corresponding to individual neurons that transport the MRC-ASM-lectin complex.

MRC-ASM-albumin

This class of agent was designed to saturate MRC-ASM type MR contrast agents with proteins prior to injection. This was done to reduce opsonization and thus produce longer blood half-lives. The result is a vascular contrast agent with eventual uptake by the RES (liver, spleen, bone marrow). Attachment of human or bovine serum albumin P-MION and PION was performed by chemisorption. Both albumins were obtained commercially (Sigma Chemicals, St. Louis, Mo.). When injected by IV, the MRC-ASM-albumin compound showed a long blood half-life making vascular imaging possible. Alternative albumin labels include but are not limited to galactosylated HSA, lactosylated HSA, and maleated HSA.

MRC-ASM-thyroglobulin

This agent was designed as an MR contrast agent for the thyroid gland to enhance detection of thyroid malignancy. The contrast agent is directed to thyroglobulin receptors. Attachment of thyroglobulin to P-MION and PION was performed by chemisorption. Thyroglobulin was obtained from a commercial source (Sigma Chemicals, St. Louis, Mo.).

PION-polysorbate

This class of agent was synthesized according to the PION protocol using 10 mL of polysorbate 20 in step one of the synthesis description. Contrast agent was injected into an animal and relaxation time measurements and MR images were obtained. Liver T2 after injection of the agent was 19.4 msec (control before injection 35.2 msec). MR imaging confirmed that this agent significantly decreases the signal intensity of liver.

PION-saponin

This class of agent was synthesized according to the PION protocol using 1 g of saponin, a glycoside, in step one of the synthesis description. Dialyzed compound (should be dialyzed against water instead of TSB) had an R2 relativity of 55.1 $(mMsec)^{-1}$. The same method can be applied to bind a large variety of glycosides or hormones to MRC's.

Toxicity

Clinical trials have shown a dose related side effect on blood pressure when iron oxides are injected into humans. Our current studies indicate that the major determinants of cardiovascular toxicity are hypoosmolarity and pH related side effects. Because these effects are undesirable, MRC-ASM type contrast agents as taught herein are made isoosmolar with human serum and are buffered a neutral pH before IV injection.

Osmotoxicity

EXAMPLE 19

The following experiments were performed to determine the effect of osmolarity of MRC-ASM solutions on blood pressure. Aliquots of 20 ml of a MRC-ASM stock solution (MION) were dialyzed at 4° C. for 24 hours in 0.01M solutions of sodium citrate, acetate, borate, Tris, distilled water and TSB. Following dialysis, the concentration was adjusted to 20 μmol Fe/kg and the osmolarity of each preparation was determined to be: Tris 60 mOsm, borate 183 mOsm, citrate 87 mOsm, water 18 mOsm, TSB 290 mOsm.

Figure 8:
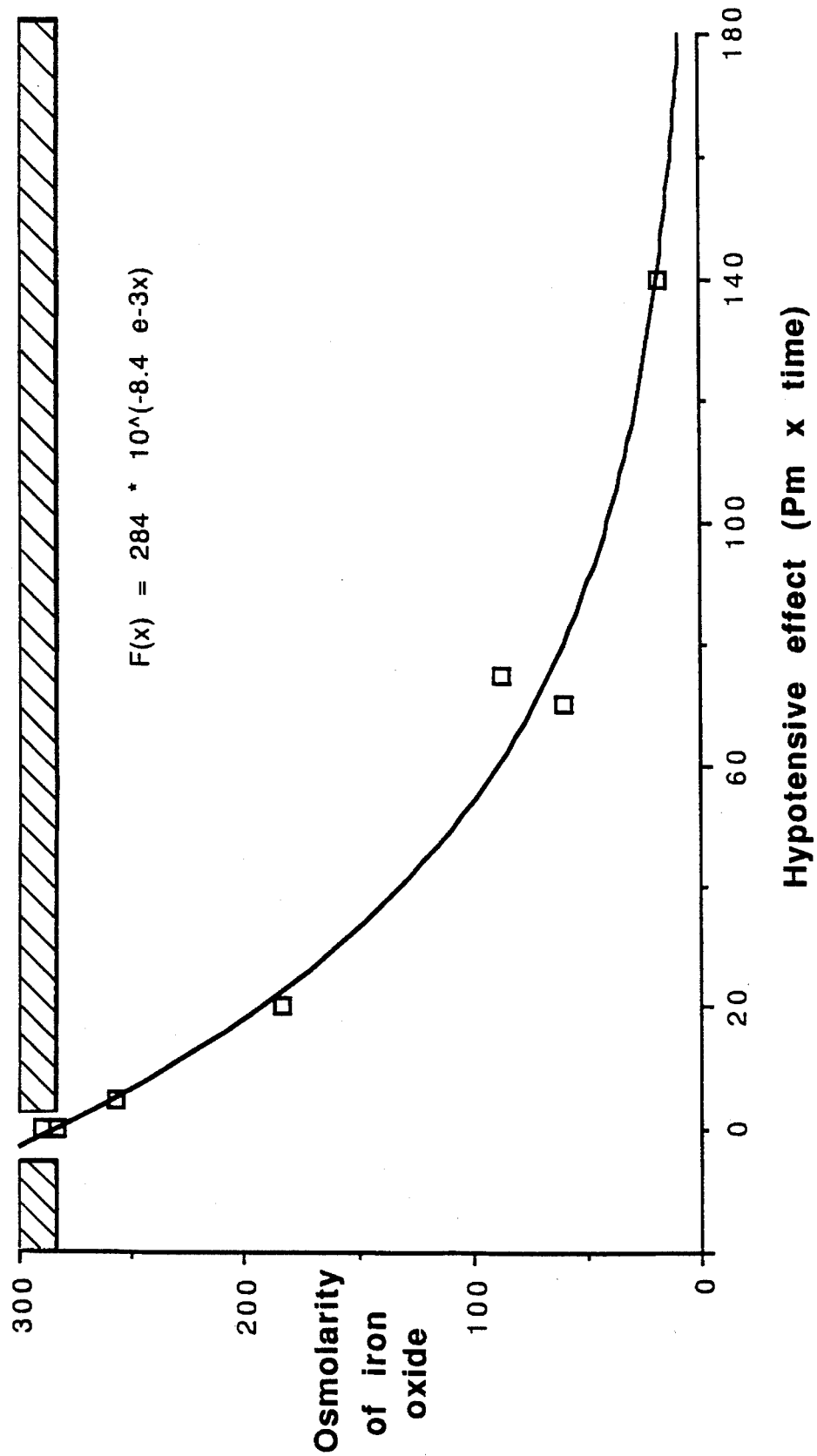
FIG. 8 is a plot of hypotensive side effect and osmolarity of an iron oxide solution.

Rabbits (5.4 k9) with femoral approach aortic catheters (anesthesia with 2.3 ml of a solution containing: ketalar 100 mg/mL+100 mg Rompun (xylazine) per small vial of ketamine) were prepared for these experiments. The arterial blood pressure was continuously recorded through the aortic catheter and decrease in systolic pressure was marked after bolus administration of 3 mL of each of the above solution. The results in FIG. 8 indicate the relationship between hypotensive side effects (x-axis) and the osmolarity (y-axis) of the administered iron oxide solution. The only MRC-ASM solution which did not show any cardiovascular side effects was the one at physiologic osmolarity (290 mOsm/L).

Preferred physiologic solutions

The following are preferred physiologic solutions to which MRC-ASM may be added to achieve isotonicity with serum.

sodium chloride (0.9% solution is isotonic)

dextrose solution (5% solution is isotonic)

Ringer's solution and lactated Ringer's solution multiple ingredient salt solutions salt meglumine solutions phosphate buffered saline sodium lactate fructose amino acid solutions pH related toxicity Unphysiologic concentrations of H+/OH− ions in injectable solutions have an adverse effects when injected IV. Because of these unwanted effects, MRC-ASM are preferably stabilized in a physiologic buffer solution. Preferred preparations are described below.

Direct side effects of unphysiological pH

Non-physiological pH (<7.2 or >7.4) is undesirable for injectable solutions because of local toxicity (phlebitis, tissue necrosis if extravasated). In addition, solutions with non-physiological pH cause disturbances in the acid/base balance. Acid base disturbances can lead to significant cardiovascular side effects.

Freshly synthesized MRC-ASM solutions prepared without a buffer solution may undergo pH drifts. Such pH drifts can be caused by slow release of OH⁻ ions from the MRC. In addition, oxidation of $Fe^{2+}$ to $Fe^{3+}$ may occur (especially by exposure to oxygen) and this reaction may also induce pH shifts. Shifts in pH are best suppressed by addition of a buffer substance to the MRC-ASM.

Side effects caused by degradation of MRC-ASM complexes at non-neutral pH

Two indirect effects have been shown to increase toxicity: a low pH (<6) dissolves MRC-ASM and high pH (>9) causes agglomeration of MRC-ASM.

Low pH dissolves ferric and ferrous ions from the MRC-ASM. IV injected free iron causes serious side effects. Besides preventing changes in pH in MRC-ASM solutions, it may be preferable to add a chelators for free iron to MRC-ASM. Preferred chelators are:

DTPA, EDTA and all analogues desferoxamine transferrin glucuronic acid, all carboxylic acid sugars High pH causes agglomeration of MRC-ASM. Larger particles are more immunogenic than small particles because of their easier recognition by the immune system. Subsequent release of vasoactive substances (e.g., slow releasing substance P, vasoactive peptides) may cause severe cardiovascular side effects.

Preferred buffer solutions

All of the buffer solutions should be complemented with ionic or non-ionic solutions to achieve isoosmolarity. Preferably the buffer solution should be inert with respect to the MRC-ASM.

Tris buffer (ph 7.2, osmolarity of 290 mOsm):

| 1. Tris base | 3.075 g |
|---|---|
| 2. NaCl | 6.24 g |
| 3. HCl | 23 mL (1N) |
| 4. H2O | add to 1000 mL |

Borate buffer (pH 8.0):

1. 19.068 g $Na_2B_2O_7$ 10 $H_2O$
2. 80 ml of HCl, 1N
3. Adjust the pH to 8.0 and fill up to 2000 ml of total volume.
4. This yields a 0.025M solution which is hypotonic and has to be adjusted with saline.

Acetate buffer (pH 7.2):

1. 7.35 g trisodium acetate
2. 10 ml of HCl, 1N
3. Adjust the pH to 7.2 and fill up to 2000 ml of total volume
4. This yields a 0.025M solution which is hypotonic and has to be adjusted with saline.

Meglumnine buffer (pH 8.5):

Described by: V. Chromy, V. Kulhanek, J. Fischer. D(-)-N-methylgtucamine buffer for pH 8.5 to 10.5 Clin Chemistry 1978;24(2):379–381

Other preferred buffers:

ammoniumncarbonate buffer (pH 9.6), ammoniumphosphate phosphate buffer (pH7.2)

sulfate buffers 1-alkylamino-1-deoxyaldose buffers (derivatives and structural analogues of meglumine buffer)

lactate buffers phosphoric acid buffers

Other Applications

Nuclear medicine imaging

A commonly encountered problem in nuclear medicine imaging is the long blood half-life of monoclonal antibodies (24–48 hours). Long blood half-life causes persistent blood pool activity obscuring localization and delaying diagnosis.

MRC-ASM-antibody complexes can be used to decrease the long blood half-life of native antibodies to several hours. This is an advantage to nuclear medicine studies in which localization of targeted radioactivity is obscured by the presence of radioisotopes in the blood pool for long periods of time. Furthermore, more than one Fab can be bound per MRC-ASM, increasing the binding affinity of the complex to antigenic sites as compared to that of free antibody for the same concentration of protein.

Laboratory techniques

Various laboratory techniques were developed to test the efficacy of MRC-ASM. These techniques allow prediction of the behavior of receptor and immunospecific MR contrast agents in the human body, obviating the need for clinical experiments.

Receptor affinity assay

Figure 9:
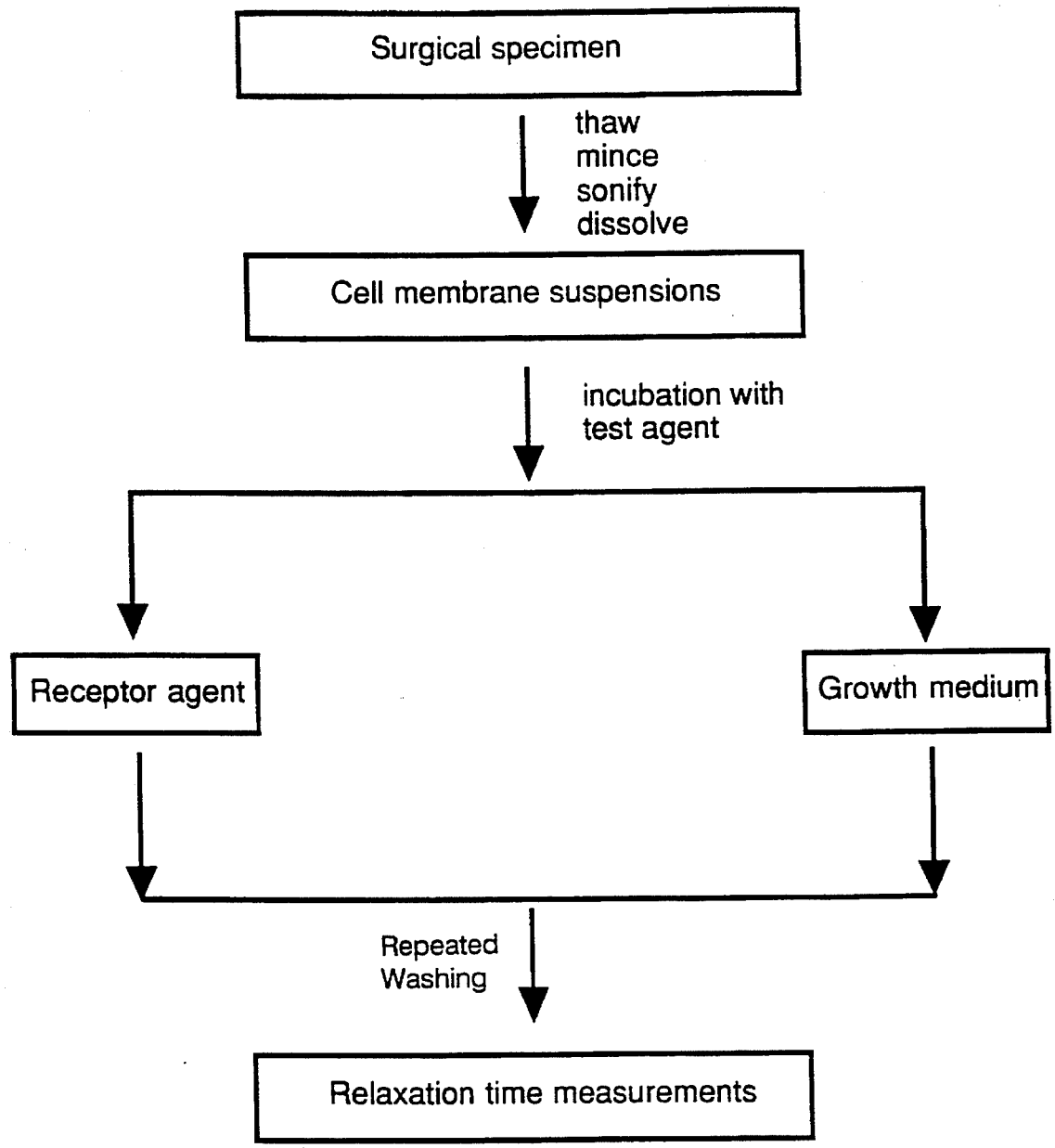
FIG. 9 is a flow chart of a receptor affinity assay.

Isolated cell membrane experiments were performed to assess the receptor-mediated binding of receptor agents. Frozen human tumor and liver specimens were thawed in complete growth medium, minced through a wire mesh, and incubated with 0.3 mg/ml of collagenase in complete growth medium. After centrifugation at 1500 rpm for 15 minutes, the supernatant containing cell membranes were incubated with 10 mol Fe with receptor agents. After washing to remove free unbound iron oxide particles, the T2 relaxation time values of these aqueous membrane solutions were determined. T2 relaxation times of cell membrane solutions incubated with receptor agents were significantly shorter than those for control agents. Specific uptake of the receptor agents as determined by relaxation times, can be comparatively blocked by concomitant administration of a receptor agonist. An assay flow chart appears in FIG. 9.

Histologic receptor assay

Figure 10:
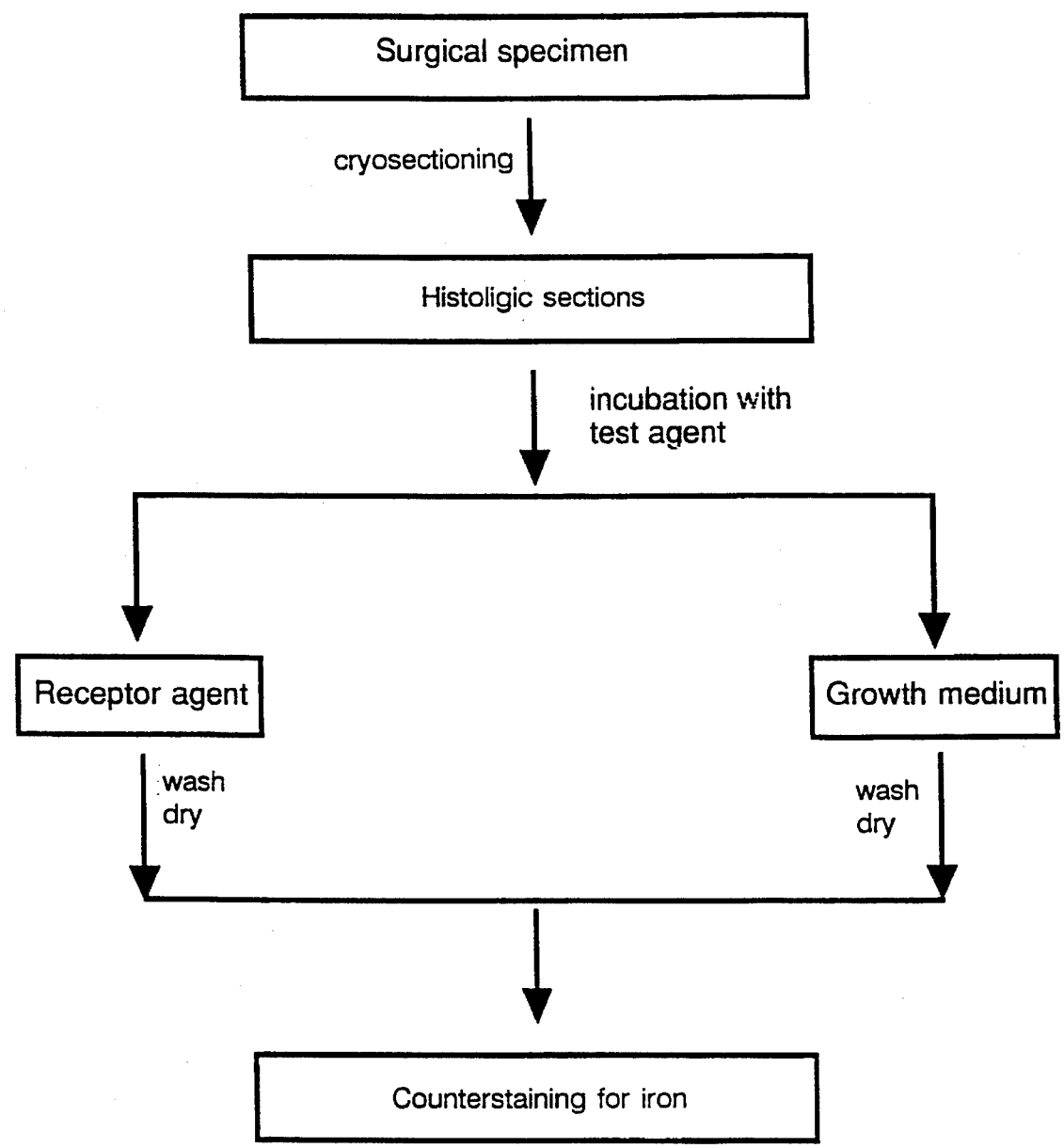
FIG. 10 is a flow chart of a histological receptor assay.

In vitro experiments assessing the degree of binding of receptor and immunospecific MR contrast agents have been performed. Cryosectioned sections of human or animal tissue are dried on glass microscope slides at room temperature. Subsequently, MR receptor agents are spread on the glass microscope slide for several seconds to minutes (depending on receptor or antigen density), are then gently washed off. Slides are then counterstained for iron by the Prussian blue method. Deposits of blue stain indicate attachment of the MRC-ASM-TSM complex to the tissue. Parallel control experiments can be performed with non-receptor or non-immunospecific control agents. An assay flow chart appears in FIG. 10.

Other embodiments are in the following claims.

I claim:

1. A liquid comprising monocrystalline superparamagnetic iron oxide particles, each particle containing a magnetically responsive core (MRC), to be used for investigation of biological objects wherein said MRC is a single crystal in at least 50% of the particles in the liquid, and is monocrystalline or polycrystalline in the remaining particles in the liquid.

2. The liquid of claim 1 wherein said liquid is in the form of a stabilized colloidal solution.

3. The liquid of claim 2 wherein said particles have attached thereto an anchored surface molecule (ASM) which increases the aqueous solubility of said particles and stabilizes an aqueous solution of said particles.

4. The liquid of claim 3 wherein said ASM is a dextran, modified dextran, or polymer.

5. The liquid of claim 1 wherein said particles are of a size that, when administered to a human patient, said particles can pass through a wall of a human capillary while retaining their superparamagnetic ability.

6. The liquid of claim 1 wherein said liquid exhibits a pharmaceutically acceptable level of toxicity.

7. The liquid of claim 1 wherein said magnetically responsive cores of said superparamagnetic particles have an average diameter of between 1 and 10 nanometers as measured by electron microscopy.

8. The liquid of claim 1 wherein at least some of said particles are covalently or noncovalently coupled to one or more specific affinity labels that target said particles to specific biological tissues.

9. The liquid of claim 8 wherein said specific affinity label comprises an antibody or binding fragment thereof.

10. The liquid of claim 9 wherein said antibody fragment is an $F(ab')_2$ fragment to myosin.

11. The liquid of claim 8 wherein said specific affinity label comprises a ligand for a cell receptor.

12. The liquid of claim 8 wherein said specific affinity label targets cell surfaces.

13. The liquid of claim 8 wherein said specific affinity label is a lipid.

14. The liquid of claim 8 wherein said specific affinity label is a polysaccharide.

15. The liquid of claim 14 wherein said specific affinity label is selected from the group consisting of hydroxyethyl starch, dextran, aldehyde dextran, and aminated dextran.

16. The liquid of claim 8 wherein said specific affinity label comprises an antigen.

17. The liquid of claim 8 wherein said specific affinity label comprises a cell receptor.

18. The liquid of claim 8 wherein said specific affinity label is a red blood cell or white blood cell.

19. A diagnostic kit comprising, in separate containers, (a) the liquid of claim 1; and (b) a specific affinity label which specifically binds to said particles to target said particles to a specific biological tissue when said liquid and said specific affinity label are mixed.

20. The kit of claim 19 wherein said liquid and said specific affinity label have been lyophilized for storage.

21. A liquid in the form of a stabilized colloidal solution comprising monocrystalline superparamagnetic iron oxide particles each particle containing a magnetically responsive core (MRC) whose average diameter is between 1 and 10 nanometers as measured by electron microscopy, wherein said MRC is a single crystal in at least 50% of said particles in said liquid, and is monocrystalline or polycrystalline in the remaining particles in the liquid.

22. The liquid of claim 21 wherein at least some of said monocrystalline particles are covalently or non-covalently coupled to one or more specific affinity labels that target said particles to specific biological tissues.

23. A diagnostic agent comprising a liquid, said liquid comprising monocrystalline superparamagnetic iron oxide particles, each particle having a transverse relaxivity greater than about 10 $(mM\ sec)^{-1}$, each particle containing a magnetically responsive core (MRC), wherein said MRC is a single crystal in at least 50% of the particles in the liquid, and is monocrystalline or polycrystalline in the remaining particles in the liquid, and each particle having anchored thereto an anchored surface molecule (ASM) which increases the solubility of said magnetic particle in an aqueous solution and stabilizes an aqueous solution of said particle.

24. The agent of claim 23 wherein said ASM is a polymer.

25. The agent of claim 24 wherein said polymer is a synthetic organic polymer.

26. The agent of claim 24 wherein said polymer is an anionic polymer.

27. The agent of claim 24 wherein said polymer is a polysaccharide or a derivative thereof.

28. The agent of claim 27 wherein said polysaccharide is a dextran or a derivative or modification thereof.

29. The agent of claim 24 wherein said ASM is bonded non-covalently to said particle.

30. The agent of claim 24 wherein said ASM is bonded covalently to said particle.

31. The agent of claim 24 wherein said ASM is water-soluble.

32. The agent of claim 24 wherein said particle is coupled to a specific affinity label that targets said particles to a specific biological tissue.

* * * * *

UNITED STATES PATENT AND TRADEMARK OFFICE
CERTIFICATE OF CORRECTION

PATENT NO. : 5,492,814

DATED : February 20, 1996

INVENTOR(S) : Ralph Weissleder

Figure 3:
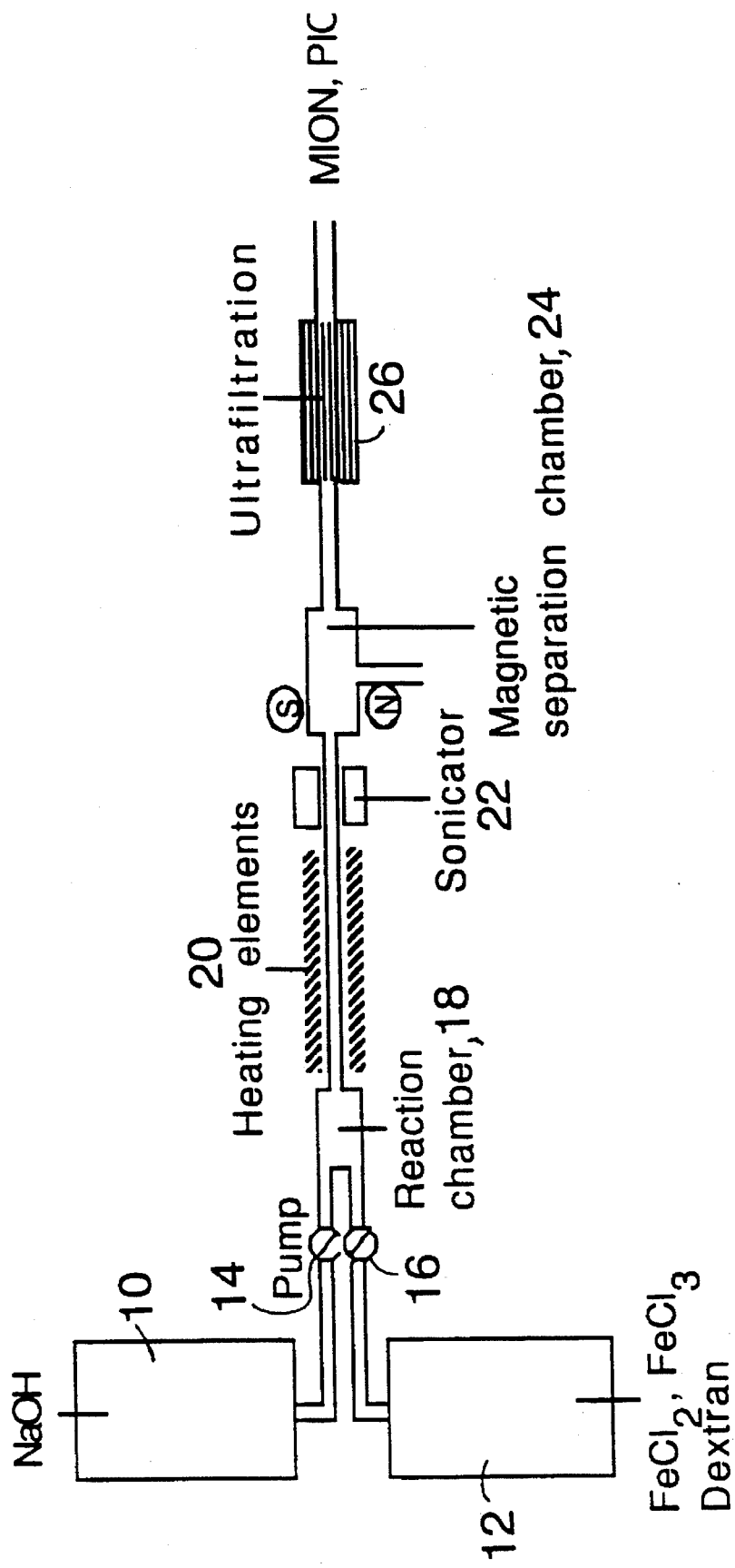
FIG. 3 is a schematic illustration of an apparatus for the continuous production of Mions and other MRC-ASM.

It is certified that error appears in the above-identified patent and that said Letters Patent is hereby corrected as shown below:

Col. 1, line 42, replace "(i.e., When" with --(i.e., when--;

Col. 2, line 8, replace "Fe+2/Fe+of4:1" with --Fe+2/Fe+3 of 4:1--;

Col. 11, line 28, replace "monotaurate" with --monolaurate--;

Col. 11, line 37, replace "proply" with --propyl--;

Col. 15, line 52, correct the spelling of "susceptibility";

Col. 19, line 10, correct the spelling of "maximum";

Col. 19, line 17, replace "nonrecated contaminants" with --nonreacted contaminants--;

Col. 19, line 18, correct the spelling of "monocrystalline";

Col. 19, line 49, correct the spelling of "hydroxytoluene";

Col. 21, line 45, replace "FIG. 4" with --FIG. 3--;

UNITED STATES PATENT AND TRADEMARK OFFICE
CERTIFICATE OF CORRECTION

PATENT NO. : 5,492,814

DATED : February 20, 1996

INVENTOR(S) : Ralph Weissleder

It is certified that error appears in the above-identified patent and that said Letters Patent is hereby corrected as shown below:

Col. 22, line 61, correct the spelling of "diacetylene";

Col. 24, line 18, correct the formula as follows: "$N_yFe_{2-y}O_3)b,$";

Col. 25, line 31, correct the spelling of "AMICON";

Col. 25, line 48, correct the spelling of "presence";

Col. 28, line 17, replace "(ASP)" with --(ASF)--;

Col. 30, line 64, replace "form" to --from--;

Col. 34, line 55, delete "an";

Col. 38, claim 22, line 10, delete "monocrystalline".

Signed and Sealed this

Ninth Day of July, 1996

Attest:

*Attesting Officer*

BRUCE LEHMAN

*Commissioner of Patents and Trademarks*